United States Patent
Higgins et al.

(10) Patent No.: US 11,826,153 B2
(45) Date of Patent: Nov. 28, 2023

(54) ATRIAL ARRHYTHMIA EPISODE DETECTION IN A CARDIAC MEDICAL DEVICE

(71) Applicant: Medtronic, Inc., Minneapolis, MN (US)

(72) Inventors: Elise J. Higgins, St. Paul, MN (US); Mark L. Brown, North Oaks, MN (US); Jian Cao, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/148,040

(22) Filed: Dec. 29, 2022

(65) Prior Publication Data

US 2023/0136836 A1    May 4, 2023

Related U.S. Application Data

(63) Continuation of application No. 16/805,057, filed on Feb. 28, 2020, now Pat. No. 11,576,607, which is a
(Continued)

(51) Int. Cl.
*A61B 5/36*    (2021.01)
*A61B 5/363*    (2021.01)
(Continued)

(52) U.S. Cl.
CPC .......... *A61B 5/363* (2021.01); *A61B 5/02405* (2013.01); *A61B 5/287* (2021.01);
(Continued)

(58) Field of Classification Search
None
See application file for complete search history.

(56) References Cited

U.S. PATENT DOCUMENTS

| 4,226,245 A | 10/1980 | Bennett |
| 4,374,382 A | 2/1983 | Markowitz |

(Continued)

FOREIGN PATENT DOCUMENTS

| CN | 103354730 A | 10/2013 |
| CN | 104363823 A | 2/2015 |

(Continued)

OTHER PUBLICATIONS

Zhang et al., "Method and Apparatus for Beat Acquisition During Template Generation in a Medical Device Having Dual Sensing Vectors", U.S. Appl. No. 14/604,111, filed Jan. 23, 2015, 77 pages.
(Continued)

*Primary Examiner* — Ankit D Tejani

(57) ABSTRACT

A medical device is configured to detect an atrial tachyarrhythmia episode. The device senses a cardiac signal, identifies R-waves in the cardiac signal attendant ventricular depolarizations and determines classification factors from the R-waves identified over a predetermined time period. The device classifies the predetermined time period as one of unclassified, atrial tachyarrhythmia and non-atrial tachyarrhythmia by comparing the determined classification factors to classification criteria. A classification criterion is adjusted from a first classification criterion to a second classification criterion after at least one time period being classified as atrial tachyarrhythmia. An atrial tachyarrhythmia episode is detected by the device in response to at least one subsequent time period being classified as atrial tachyarrhythmia based on the adjusted classification criterion.

21 Claims, 14 Drawing Sheets

Related U.S. Application Data continuation of application No. 16/051,779, filed on Aug. 1, 2018, now Pat. No. 10,575,748, which is a continuation of application No. 15/084,511, filed on Mar. 30, 2016, now Pat. No. 10,045,710.

(51) Int. Cl.
| | |
|---|---|
| *A61B 5/00* | (2006.01) |
| *A61B 5/024* | (2006.01) |
| *A61B 5/287* | (2021.01) |
| *A61B 5/316* | (2021.01) |
| *A61B 5/352* | (2021.01) |
| *A61B 5/361* | (2021.01) |
| *A61N 1/39* | (2006.01) |
| *A61B 5/366* | (2021.01) |

(52) U.S. Cl.
CPC ............. *A61B 5/316* (2021.01); *A61B 5/352* (2021.01); *A61B 5/361* (2021.01); *A61B 5/7264* (2013.01); *A61N 1/3925* (2013.01); *A61N 1/3956* (2013.01); *A61N 1/3987* (2013.01); *A61B 5/002* (2013.01); *A61B 5/366* (2021.01); *A61B 5/4836* (2013.01); *A61B 2560/028* (2013.01); *A61N 1/395* (2013.01); *A61N 1/39622* (2017.08)

(56) References Cited

U.S. PATENT DOCUMENTS

| | | |
|---|---|---|
| 4,721,114 A | 1/1988 | DuFault et al. |
| 5,117,824 A | 6/1992 | Keimel et al. |
| 5,193,535 A | 3/1993 | Bardy et al. |
| 5,292,338 A | 3/1994 | Bardy |
| 5,312,445 A | 5/1994 | Nappholz et al. |
| 5,334,221 A | 8/1994 | Bardy |
| 5,458,623 A | 10/1995 | Lu et al. |
| 5,545,186 A | 8/1996 | Olson et al. |
| 5,609,157 A | 3/1997 | Panescu et al. |
| 5,609,158 A | 3/1997 | Chan |
| 5,622,178 A | 4/1997 | Gilham |
| 5,755,739 A | 5/1998 | Sun et al. |
| 5,782,888 A | 7/1998 | Sun et al. |
| 5,817,134 A | 10/1998 | Greenhut et al. |
| 6,067,473 A | 5/2000 | Greeninger et al. |
| 6,393,316 B1 | 5/2002 | Gillberg et al. |
| 6,412,490 B1 | 7/2002 | Lee |
| 6,418,346 B1 | 7/2002 | Nelson et al. |
| 6,442,433 B1 | 8/2002 | Linberg |
| 6,470,210 B1 | 10/2002 | Chen et al. |
| 6,480,745 B2 | 11/2002 | Nelson et al. |
| 6,516,225 B1 | 2/2003 | Florio |
| 6,599,250 B2 | 7/2003 | Webb et al. |
| 6,745,068 B2 | 6/2004 | Koyrakh et al. |
| 6,865,414 B1 | 3/2005 | Levine |
| 6,871,089 B2 | 3/2005 | Korzinov et al. |
| 6,895,272 B2 | 5/2005 | Seim et al. |
| 6,904,315 B2 | 6/2005 | Panken et al. |
| 6,904,319 B2 | 6/2005 | Seim et al. |
| 6,912,418 B1 | 6/2005 | Florio |
| 6,922,584 B2 | 7/2005 | Wang et al. |
| 6,931,273 B2 | 8/2005 | Groenewegen et al. |
| 7,027,858 B2 | 4/2006 | Cao et al. |
| 7,031,765 B2 | 4/2006 | Ritscher et al. |
| 7,062,315 B2 | 6/2006 | Koyrakh et al. |
| 7,092,761 B1 | 8/2006 | Cappa et al. |
| 7,120,485 B2 | 10/2006 | Glass et al. |
| 7,139,604 B1 | 11/2006 | Mouchawar et al. |
| 7,146,206 B2 | 12/2006 | Glass et al. |
| 7,184,815 B2 | 2/2007 | Kim et al. |
| 7,187,965 B2 | 3/2007 | Bischoff et al. |
| 7,188,965 B2 | 3/2007 | Chang et al. |
| 7,242,978 B2 | 7/2007 | Cao et al. |
| 7,267,368 B2 | 9/2007 | Lagsdin |
| 7,308,308 B1 | 12/2007 | Xi et al. |
| 7,333,855 B2 | 2/2008 | Gunderson et al. |
| 7,412,282 B2 | 8/2008 | Houben |
| 7,509,160 B2 | 3/2009 | Bischoff et al. |
| 7,515,956 B2 | 4/2009 | Thompson |
| 7,532,928 B2 | 5/2009 | Lang |
| 7,537,569 B2 | 5/2009 | Sarkar et al. |
| 7,561,911 B2 | 7/2009 | Cao et al. |
| 7,570,990 B2 | 8/2009 | Faber et al. |
| 7,580,748 B2 | 8/2009 | Garner et al. |
| 7,593,766 B2 | 9/2009 | Faber et al. |
| 7,596,405 B2 | 9/2009 | Kurzweil et al. |
| 7,623,911 B2 | 11/2009 | Sarkar et al. |
| 7,627,368 B2 | 12/2009 | Houben et al. |
| 7,634,310 B2 | 12/2009 | Lee et al. |
| 7,640,054 B2 | 12/2009 | Koyrakh et al. |
| 7,657,305 B2 | 2/2010 | Nigam |
| 7,657,307 B2 | 2/2010 | Van Dam et al. |
| 7,706,869 B2 | 4/2010 | Cao et al. |
| 7,729,754 B2 | 6/2010 | Cao et al. |
| 7,826,893 B2 | 11/2010 | Cao et al. |
| 7,831,304 B2 | 11/2010 | Cao et al. |
| 7,983,742 B2 | 7/2011 | Starc |
| 7,996,070 B2 | 8/2011 | van Dam et al. |
| 8,000,778 B2 | 8/2011 | Seim et al. |
| 8,064,998 B2 | 11/2011 | Good et al. |
| 8,155,735 B2 | 4/2012 | Bashour et al. |
| 8,195,280 B2 | 6/2012 | Van Dam et al. |
| 8,233,980 B2 | 7/2012 | Pei |
| 8,265,753 B2 | 9/2012 | Higham et al. |
| 8,280,510 B2 | 10/2012 | Dyjach et al. |
| 8,285,377 B2 | 10/2012 | Rosenberg et al. |
| 8,412,316 B2 | 4/2013 | Seim et al. |
| 8,428,697 B2 | 4/2013 | Zhang et al. |
| 8,428,705 B2 | 4/2013 | Kurzweil et al. |
| 8,437,851 B2 | 5/2013 | Corbucci et al. |
| 8,521,268 B2 | 8/2013 | Zhang et al. |
| 8,548,573 B2 | 10/2013 | Keefe |
| 8,560,058 B2 | 10/2013 | Babaeizadeh et al. |
| 8,588,895 B2 | 11/2013 | Sanghera et al. |
| 8,639,316 B2 | 1/2014 | Sarkar |
| 8,688,469 B2 | 4/2014 | Ziegler et al. |
| 8,718,750 B2 | 5/2014 | Lian et al. |
| 8,744,559 B2 | 6/2014 | Houben et al. |
| 8,922,963 B2 | 12/2014 | Braun |
| 8,977,350 B2 | 3/2015 | Sarkar et al. |
| 9,031,645 B2 | 5/2015 | Houben et al. |
| 9,486,155 B2 | 11/2016 | Sarkar et al. |
| 9,561,005 B2 | 2/2017 | Zhang |
| 9,603,543 B2 | 3/2017 | Sarkar et al. |
| 9,675,261 B2 | 6/2017 | Cao et al. |
| 9,675,269 B2 | 6/2017 | Sarkar et al. |
| 10,045,710 B2 | 8/2018 | Higgins et al. |
| 2002/0120206 A1 | 8/2002 | Taha et al. |
| 2003/0144597 A1 | 7/2003 | Bock |
| 2004/0171958 A1 | 9/2004 | Fitts et al. |
| 2004/0249420 A1 | 12/2004 | Olson et al. |
| 2005/0065564 A1 | 3/2005 | Seim et al. |
| 2005/0080347 A1 | 4/2005 | Sheth et al. |
| 2006/0074332 A1 | 4/2006 | Bischoff et al. |
| 2006/0079797 A1 | 4/2006 | Bischoff et al. |
| 2006/0079798 A1 | 4/2006 | Bischoff et al. |
| 2006/0106323 A1 | 5/2006 | Bischoff et al. |
| 2007/0142866 A1 | 6/2007 | Li et al. |
| 2007/0219456 A1 | 9/2007 | Thompson |
| 2007/0232944 A1 | 10/2007 | Ghanem et al. |
| 2008/0103540 A1 | 5/2008 | Cao |
| 2008/0147133 A1 | 6/2008 | Garner et al. |
| 2008/0154318 A1 | 6/2008 | Albus et al. |
| 2008/0161703 A1 | 7/2008 | Houben et al. |
| 2009/0216144 A1 | 8/2009 | Hopenfeld |
| 2009/0270747 A1 | 10/2009 | van Dam et al. |
| 2009/0299205 A1 | 12/2009 | Chow |
| 2010/0030293 A1 | 2/2010 | Sarkar et al. |
| 2010/0274149 A1 | 10/2010 | Li et al. |
| 2011/0125206 A1 | 5/2011 | Bornzin et al. |
| 2011/0301661 A1 | 12/2011 | Seim et al. |
| 2011/0319949 A1 | 12/2011 | Bardy et al. |
| 2012/0004566 A1 | 1/2012 | Zhang et al. |

(56) References Cited

U.S. PATENT DOCUMENTS

| | | |
|---|---|---|
| 2012/0089032 A1 | 4/2012 | Park et al. |
| 2012/0123232 A1 | 5/2012 | Najarian et al. |
| 2012/0226179 A1 | 9/2012 | Stadler et al. |
| 2012/0238891 A1 | 9/2012 | Sarkar et al. |
| 2012/0238892 A1 | 9/2012 | Sarkar |
| 2012/0330171 A1 | 12/2012 | Zhang et al. |
| 2013/0006319 A1 | 1/2013 | Doerr |
| 2013/0041273 A1 | 2/2013 | Houben et al. |
| 2013/0172765 A1 | 7/2013 | Stewart |
| 2014/0148717 A1 | 5/2014 | Eberle et al. |
| 2014/0155722 A1 | 6/2014 | Greenspan et al. |
| 2014/0257421 A1 | 9/2014 | Sanghera et al. |
| 2014/0276154 A1 | 9/2014 | Katra et al. |
| 2014/0350422 A1 | 11/2014 | Stewart |
| 2014/0378851 A1 | 12/2014 | Frei et al. |
| 2015/0057488 A1 | 2/2015 | Yomtov |
| 2015/0073295 A1 | 3/2015 | Gordon et al. |
| 2015/0080752 A1 | 3/2015 | Lian et al. |
| 2015/0088216 A1 | 3/2015 | Gordon et al. |
| 2015/0105681 A1 | 4/2015 | Bonan et al. |
| 2015/0230722 A1 | 8/2015 | Sarkar et al. |
| 2015/0305642 A1 | 10/2015 | Reinke et al. |
| 2015/0306375 A1 | 10/2015 | Marshall et al. |
| 2015/0306410 A1 | 10/2015 | Marshall et al. |
| 2016/0113534 A1 | 4/2016 | Cao et al. |
| 2016/0113537 A1 | 4/2016 | Cao et al. |
| 2016/0113577 A1 | 4/2016 | Cao et al. |
| 2016/0158567 A1 | 6/2016 | Marshall et al. |
| 2016/0213273 A1 | 7/2016 | Cao et al. |
| 2016/0213274 A1 | 7/2016 | Cao et al. |
| 2016/0213275 A1 | 7/2016 | Cao et al. |
| 2016/0213941 A1 | 7/2016 | Zhang |
| 2016/0235317 A1 | 8/2016 | Sarkar et al. |
| 2016/0235318 A1 | 8/2016 | Sarkar |
| 2016/0255321 A1 | 9/2016 | Chen et al. |
| 2018/0028086 A1 | 2/2018 | Cao et al. |

FOREIGN PATENT DOCUMENTS

| | | |
|---|---|---|
| CN | 104955387 A | 9/2015 |
| CN | 105147278 A | 12/2015 |
| EP | 0617980 B1 | 10/1994 |
| EP | 2572634 A1 | 3/2013 |
| EP | 2796165 A1 | 10/2014 |
| WO | 9809241 A1 | 3/1998 |
| WO | 200180042 A1 | 10/2001 |
| WO | 2004108212 A2 | 12/2004 |
| WO | 2012058398 A1 | 5/2012 |

OTHER PUBLICATIONS

Pürerfellner et al., "P-Wave Evidence as a Method for Improving Algorithm to Detect Atrial Fibrillation in Insertable Cardiac Monitors", Heart Rhythm, vol. 11, No. 9, Sep. 2014, 9 pages.

(PCT/US2017/020874) PCT Notification of Transmittal of the International Search Report and the Written Opinion of the International Searching Authority, dated May 15, 2017, 14 pages.

ATRIAL ARRHYTHMIA EPISODE DETECTION IN A CARDIAC MEDICAL DEVICE

REFERENCE TO RELATED APPLICATION

This application is a continuation application of pending U.S. patent application Ser. No. 16/805,057, filed on Feb. 28, 2020 (published as U.S. Pub. No. 2020/0196899), which is a continuation application of pending U.S. patent application Ser. No. 16/051,779, filed on Aug. 1, 2018 (granted as U.S. Pat. No. 10,575,748), which is a continuation application of U.S. patent application Ser. No. 15/084,511, filed on Mar. 30, 2016 (granted as U.S. Pat. No. 10,045,710), the content of all of which is incorporated herein by reference in their entirety.

TECHNICAL FIELD

The disclosure relates generally to cardiac medical devices and, in particular, to a cardiac medical device and method for detecting atrial arrhythmia episodes from sensed cardiac electrical signals.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

As more serious consequences of persistent atrial arrhythmias have come to be understood, such as an associated risk of relatively more serious ventricular arrhythmias and stroke, there is a growing interest in monitoring and treating atrial arrhythmias. Implantable cardiac monitors and implantable cardioverter defibrillators (ICDs) may be configured to acquire cardiac electrical signals that can be analyzed for detecting atrial arrhythmias.

SUMMARY

In general, the disclosure is directed to techniques for detecting cardiac events, more specifically atrial tachyarrhythmia episodes, by a medical device. A medical device operating according to the techniques disclosed herein analyzes a cardiac electrical signal over a plurality of time periods and classifies each of the time periods based on characteristics of the cardiac electrical signal, such as characteristics of the RR-intervals occurring during each of the plurality of time periods. The device may adjust a threshold for classifying the cardiac signal for at least a portion of the time periods. An atrial tachyarrhythmia may be detected when a predetermined number of time periods are classified as atrial tachyarrhythmia, which may include at least one time period before the threshold adjustment and one or more time periods after the threshold adjustment.

In one example, the disclosure provides a method of detecting an atrial tachyarrhythmia episode in a medical device. The method comprises sensing a cardiac signal and identifying R-waves in the cardiac signal attendant ventricular depolarizations. The method also includes determining classification factors from the R-waves identified over a first predetermined time period and classifying the first predetermined time period as atrial tachyarrhythmia based on comparing the determined classification factors to classification criteria. The method further includes adjusting a classification criterion of the classification criteria from a first classification criterion to a second classification criterion after classifying the first time period as atrial tachyarrhythmia, classifying at least one subsequent time period as atrial tachyarrhythmia by comparing classification factors determined over the subsequent time period to the adjusted classification criterion; and detecting an atrial tachyarrhythmia episode in response to at least one subsequent time period being classified as atrial tachyarrhythmia based on the adjusted classification criteria.

In another example, the disclosure provides a medical device for detecting an atrial tachyarrhythmia episode. The medical device includes sensing circuitry configured to receive a cardiac signal from a plurality of electrodes coupled to the medical device. The medical device also includes a processor configured to identify R-waves in the cardiac signal attendant ventricular depolarizations, determine classification factors from the R-waves identified over a first predetermined time period, and classify the first predetermined time period as atrial tachyarrhythmia based on comparing the determined classification factors to classification criteria. The processor is further configured to adjust a classification criterion of the classification criteria from a first classification criterion to a second classification criterion after the first time period being classified as atrial tachyarrhythmia, classify at least one subsequent time period as atrial tachyarrhythmia by comparing classification factors determined over the subsequent time period to the adjusted classification criterion, and detect an atrial tachyarrhythmia episode in response to at least one subsequent time period being classified as atrial tachyarrhythmia based on the adjusted classification criterion.

In another example, the disclosure provides a non-transitory, computer-readable storage medium storing instructions for causing a processor included in a medical device to perform a method for detecting an atrial tachyarrhythmia episode. The method comprises sensing a cardiac signal and identifying R-waves in the cardiac signal attendant ventricular depolarizations. The method also includes determining classification factors from the R-waves identified over a first predetermined time period and classifying the first predetermined time period as atrial tachyarrhythmia based on comparing the determined classification factors to classification criteria. The method further includes adjusting a classification criterion of the classification criteria from a first classification criterion to a second classification criterion after classifying the first time period as atrial tachyarrhythmia, classifying at least one subsequent time period as atrial tachyarrhythmia by comparing classification factors determined over the subsequent time period to the adjusted classification criterion; and detecting an atrial tachyarrhythmia episode in response to at least one subsequent time period being classified as atrial tachyarrhythmia based on the adjusted classification criteria.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
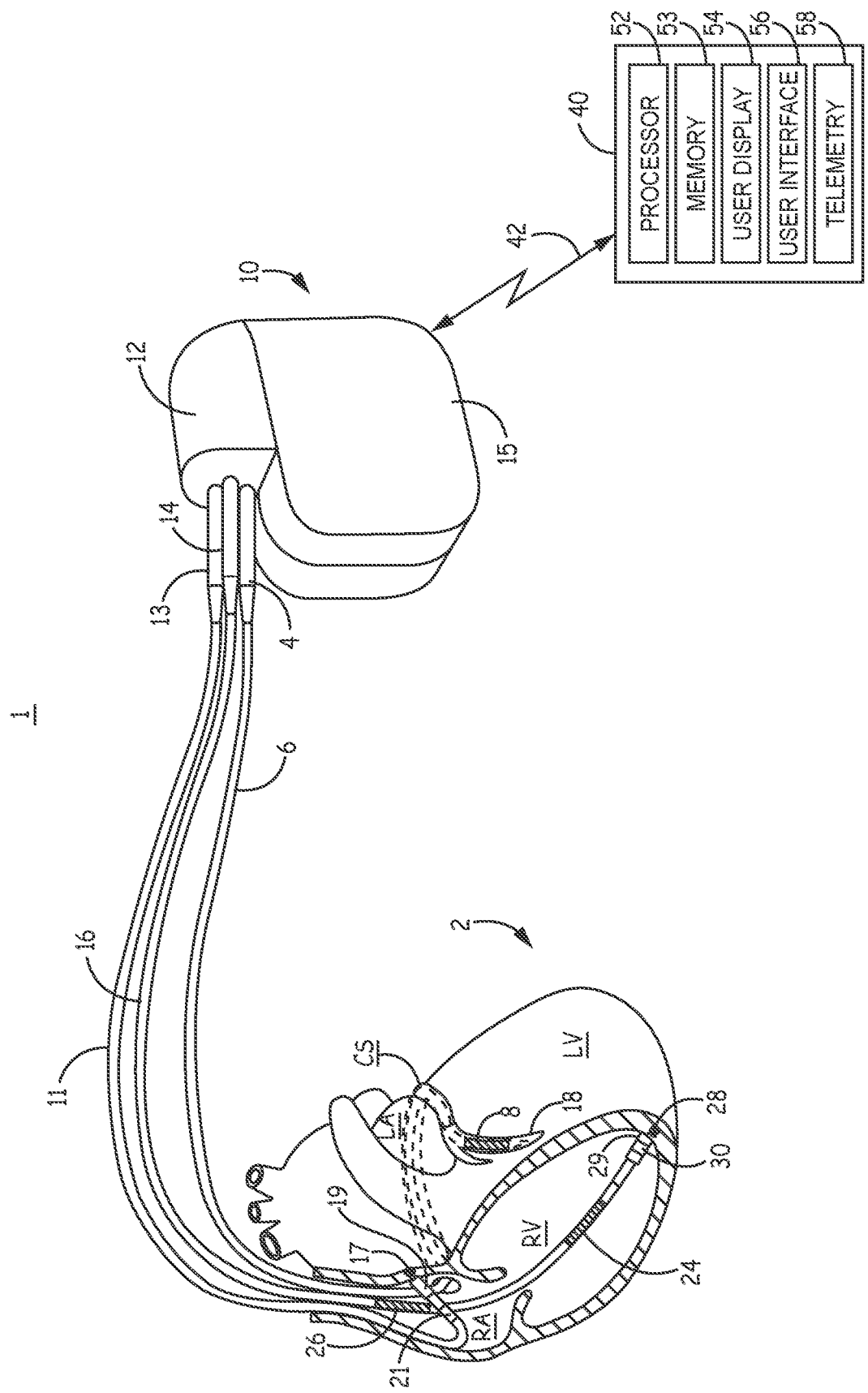
FIG. 1A is a conceptual diagram of an implantable medical device (IMD) system for detecting atrial arrhythmias according to one example.

In the following description, references are made to illustrative embodiments for carrying out the methods described herein. It is understood that other embodiments may be utilized without departing from the scope of the disclosure.

In various examples, a cardiac electrical signal is used for determining successive ventricular cycle lengths for use in detecting atrial arrhythmias. Ventricular cycle lengths may be determined as intervals between successive R-waves that are sensed from the cardiac electrical signal and attendant to the depolarization of the ventricles. The differences between successive RR intervals (RRIs) are analyzed for determining evidence of atrial tachyarrhythmia, e.g., atrial fibrillation. As described herein, a time period of the cardiac signal may be classified as AF, non-AF, or unclassified based on an analysis of the RRIs and other factors. When a predetermined number of time periods of the cardiac signal are classified as AF, a medical device operating according to the techniques disclosed herein may detect AF. The device, however, may adjust a classification criterion applied for classifying a time period of the cardiac signal prior to detecting AF and detect AF based on the adjusted classification criterion applied for classifying subsequent time periods.

Aspects of the methods described herein can be incorporated in a variety of implantable or external medical devices having cardiac signal monitoring capabilities, which may or may not include therapy delivery capabilities. Such devices include single chamber, dual chamber or bi-ventricular pacing systems or ICDs that sense the R-waves and deliver an electrical stimulation therapy to the ventricles. The atrial arrhythmia detection methods presently disclosed may also be incorporated in implantable cardiac monitors having implantable electrodes or external cardiac monitors having electrocardiogram (ECG) electrodes coupled to the patient's skin to detect R-waves, e.g., Holter monitors, or within computerized systems that analyze pre-recorded ECG or cardiac electrogram (EGM) data. Embodiments may further be implemented in a patient monitoring system, such as a centralized computer system which processes cardiac electrical signals and other data sent to it by implantable or wearable monitoring devices.

FIG. 1 is a conceptual diagram of an implantable medical device (IMD) system 1 for detecting atrial arrhythmias according to one example. The IMD system 1 of FIG. 1 includes an implantable cardioverter defibrillator (ICD) 10 coupled to a patient's heart 2 via transvenous electrical leads 6, 11, and 16. ICD 10 includes a connector block 12 that may be configured to receive the proximal ends of a right ventricular (RV) lead 16, a right atrial (RA) lead 11 and a coronary sinus (CS) lead 6, which are advanced transvenously for positioning electrodes for sensing and stimulation in three or all four heart chambers.

RV lead 16 is positioned such that its distal end is in the right ventricle for sensing RV cardiac signals and delivering pacing or shocking pulses in the right ventricle. For these purposes, RV lead 16 is equipped with pacing and sensing electrodes shown as a ring electrode 30 and a tip electrode 28. In some examples, tip electrode 28 is an extendable helix electrode mounted retractably within an electrode head 29. RV lead 16 is further shown to carry defibrillation electrodes 24 and 26, which may be elongated coil electrodes used to deliver high voltage cardioversion/defibrillation (CV/DF) electrodes. Defibrillation electrode 24 is referred to herein as the "RV defibrillation electrode" or "RV coil electrode" because it may be carried along RV lead 16 such that it is positioned substantially within the right ventricle when distal pacing and sensing electrodes 28 and 30 are positioned for pacing and sensing in the right ventricle. Defibrillation electrode 26 is referred to herein as a "superior vena cava (SVC) defibrillation electrode" or "SVC coil electrode" because it may be carried along RV lead 16 such that it is positioned at least partially along the SVC when the distal end of RV lead 16 is advanced within the right ventricle.

Figure 1B:
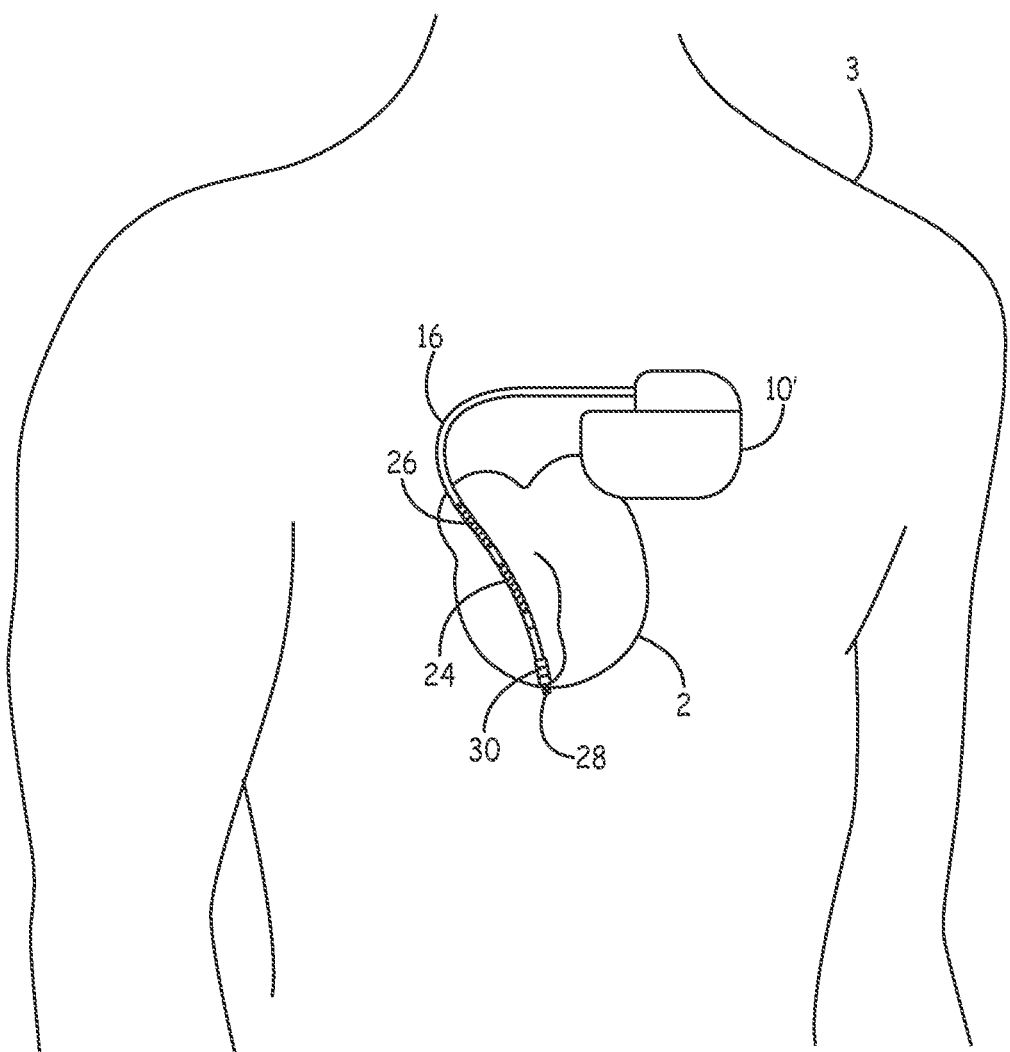
FIG. 1B is a conceptual diagram of an IMD system for detecting atrial tachyarrhythmia according to another example.

Each of electrodes 24, 26, 28 and 30 are connected to a respective insulated conductor extending within the body of lead 16. The proximal end of the insulated conductors are coupled to corresponding connectors carried by proximal lead connector 14, e.g., a DF-4 connector, at the proximal end of lead 16 for providing electrical connection to ICD 10. It is understood that although ICD 10 is illustrated in FIG. 1 as a multi-chamber chamber device coupled to RA lead 11 and CS lead 6, ICD 10 may be configured as a single chamber device coupled only to RV lead 16 as shown and described in conjunction with FIG. 1B below. The techniques disclosed herein for detecting atrial tachyarrhythmia may be successfully performed without requiring atrial signal sensing. As such, RA lead 11 is optional in some examples.

If included, RA lead 11 may be positioned such that its distal end is in the vicinity of the right atrium and the superior vena cava. Lead 11 is equipped with pacing and sensing electrodes 17 and 21 shown as a tip electrode 17, which may be an extendable helix electrode mounted retractably within electrode head 19, and a ring electrode 21 spaced proximally from tip electrode 17. The electrodes 17 and 21 provide sensing and pacing in the right atrium and are each connected to a respective insulated conductor with the body of RA lead 11. Each insulated conductor is coupled at its proximal end to connector carried by proximal lead connector 13.

CS lead 6 is also optional and not required to successfully execute the atrial tachyarrhythmia detection methods disclosed herein. When present, CS lead 6 may be advanced within the vasculature of the left side of the heart via the coronary sinus and a cardiac vein 18. CS lead 6 is shown in the embodiment of FIG. 1A as having one or more electrodes 8 that may be used in combination with either RV coil electrode 24 or the SVC coil electrode 26 for delivering electrical shocks for cardioversion and defibrillation therapies. In other examples, coronary sinus lead 6 may also be equipped with one or more electrodes 8 for use in delivering pacing and or sensing cardiac electrical signals in the left chambers of the heart, i.e., the left ventricle and/or the left atrium. The one or more electrodes 8 are coupled to respective insulated conductors within the body of CS lead 6, which provides connection to the proximal lead connector 4.

The RV pacing and sensing electrodes 28 and 30 may be used as a bipolar pair, commonly referred to as a "tip-to-ring" configuration for sensing cardiac electrical signals. Further, RV tip electrode 28 may be selected with a coil electrode 8, 24, or 26 to be used as an integrated bipolar pair, commonly referred to as a "tip-to-coil" configuration for sensing cardiac electrical signals. ICD 10 may, for example, select one or more sensing electrode vectors including a tip-to-ring sensing vector between electrodes 28 and 30 and a tip-to-coil sensing vector, e.g., between RV tip electrode 28 and SVC coil electrode 26, between RV tip electrode 28 and RV coil electrode 24, between RV ring electrode 30 and SVC coil electrode 26 or between RV ring electrode 30 and RV coil electrode 24. In some cases, any of the electrodes 24, 26, 28 or 30 carried by RV lead 16 may be selected by ICD 10 in a unipolar sensing configuration with the ICD housing 15 serving as the indifferent electrode, commonly referred to as the "can" or "case" electrode. It is recognized that numerous sensing and electrical stimulation electrode vectors may be available using the various electrodes carried by one or more of leads 6, 11 and 16 coupled to ICD 10, and ICD 10 may be configured to selectively couple one or more sensing electrode vector to sensing circuitry enclosed by housing 15, e.g., sensing circuitry including one or more amplifiers, filters, rectifiers, comparators, sense amplifiers, analog-to-digital convertors and/or other circuitry configured to acquire a cardiac electrical signal for use in detecting cardiac arrhythmias.

In other examples, the ICD housing 15 may serve as a subcutaneous defibrillation electrode in combination with one or more of the coil electrodes 8, 24 or 26 for delivering CV/DF shocks to the atria or ventricles. It is recognized that alternate lead systems may be substituted for the three lead system illustrated in FIG. 1A. While a particular multi-chamber ICD and lead system is illustrated in FIG. 1A, methodologies included in the present invention may adapted for use with any single chamber, dual chamber, or multi-chamber ICD or pacemaker system, subcutaneous implantable device, or other internal or external cardiac monitoring device.

An external device 40 is shown in telemetric communication with ICD 10 by an RF communication link 42. External device 40 is often referred to as a "programmer" because it is typically used by a physician, technician, nurse, clinician or other qualified user for programming operating parameters in ICD 10. External device 40 may be located in a clinic, hospital or other medical facility. External device 40 may alternatively be embodied as a home monitor or a handheld device that may be used in a medical facility, in the patient's home, or another location. Operating parameters, such as sensing and therapy delivery control parameters, may be programmed into ICD 10 using external device 40.

External device 40 includes a processor 52, memory 53, user display 54, user interface 56 and telemetry circuitry 58. Processor 52 controls external device operations and processes data and signals received from ICD 10. According to techniques disclosed herein, processor 52 receives sensing vector data obtained by ICD 10 and transmitted to telemetry circuitry 58 from ICD 10. As described below in conjunction with FIG. 11, ICD 10 may be configured to store cardiac signal data associated with detected atrial tachyarrhythmia episodes and transmit the cardiac signal data to external device 40. Processor 52 provides user display 54 with at least a portion of the cardiac electrical signal data for generating a display of the cardiac electrical signal detected as atrial tachyarrhythmia for observation and review by a clinician.

The user display 54 provides a display of the cardiac signal data and may include a graphical user interface that facilitates programming of one or more sensing parameters and/or atrial arrhythmia detection parameters by a user interacting with external device 40. External device 40 may display other data and information relating to ICD functions to a user for reviewing ICD operation and programmed parameters as well as cardiac electrical signals or other physiological data that is retrieved from ICD 10 during an interrogation session. User interface 56 may include a mouse, touch screen, or other pointing device, keyboard and/or keypad to enable a user to interact with external device 40 to initiate a telemetry session with ICD 10 for retrieving data from and/or transmitting data to ICD 10 and for selecting and programming desired sensing and therapy delivery control parameters into ICD 10.

Telemetry circuitry 58 includes a transceiver and antenna configured for bidirectional communication with an implantable transceiver and antenna included in ICD 10. Telemetry circuitry 58 is configured to operate in conjunction with processor 52 for encoding and decoding transmitted and received data relating to ICD functions via communication link 42. Communication link 42 may be established between ICD 10 and external device 40 using a radio frequency (RF) link such as BLUETOOTH®, Wi-Fi, Medical Implant Communication Service (MICS) or other RF bandwidth. In some examples, external device 40 may include a programming head that is placed proximate ICD 10 to establish and maintain a communication link, and in other examples external device 40 and ICD 10 may be configured to communicate using a distance telemetry algorithm and circuitry that does not require the use of a programming head and does not require user intervention to maintain a communication link.

It is contemplated that external device 40 may be in wired or wireless connection to a communications network via telemetry circuitry 58 for transferring data to a remote database or computer to allow remote management of the patient. Remote patient management systems may be configured to utilize the presently disclosed techniques to enable a clinician to review cardiac electrical signal data and atrial tachyarrhythmia episode data received from ICD 10 and to select and program control parameters transmitted to ICD 10. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of remote patient management systems that enable remote patient monitoring and device programming. Each of these patents is incorporated herein by reference in their entirety.

FIG. 1B is a conceptual diagram of a single-chamber ICD 10' coupled to RV lead 16. The techniques disclosed herein may be implemented in a single chamber ICD that is coupled only to a ventricular lead such as RV lead 16 for receiving cardiac electrical signals including at least R-waves attendant to the ventricular depolarizations of heart 2. Electrodes 28 and 30 (and/or coil electrodes 24 and 26) may be used for acquiring cardiac electrical signals needed for performing atrial tachyarrhythmia detection as described herein without requiring an atrial sensing and pacing lead 11 as shown in FIG. 1A. R-waves sensed from cardiac electrical signals obtained by ICD 10' are used for determining RR intervals (RRIs) between consecutively sensed R-waves for detecting atrial tachyarrhythmia by a processor of ICD 10' based at least in part on an analysis of the RRIs. The single chamber ICD 10' may be configured to sense cardiac electrical signals from electrodes 24, 26, 28 and/or 30, detect atrial tachyarrhythmia and provide an atrial tachyarrhythmia detection response such as storing atrial tachyarrhythmia episode data for transmission to external device 40 (shown in FIG. 1A). Single chamber ICD 10' may additionally be configured to deliver ventricular bradycardia pacing, detect ventricular tachyarrhythmias, and deliver anti-tachycardia pacing therapy and cardioversion/defibrillation shock therapies to the RV via electrodes 24, 26, 28 and/or 30 carried by lead 16.

Figure 1C:
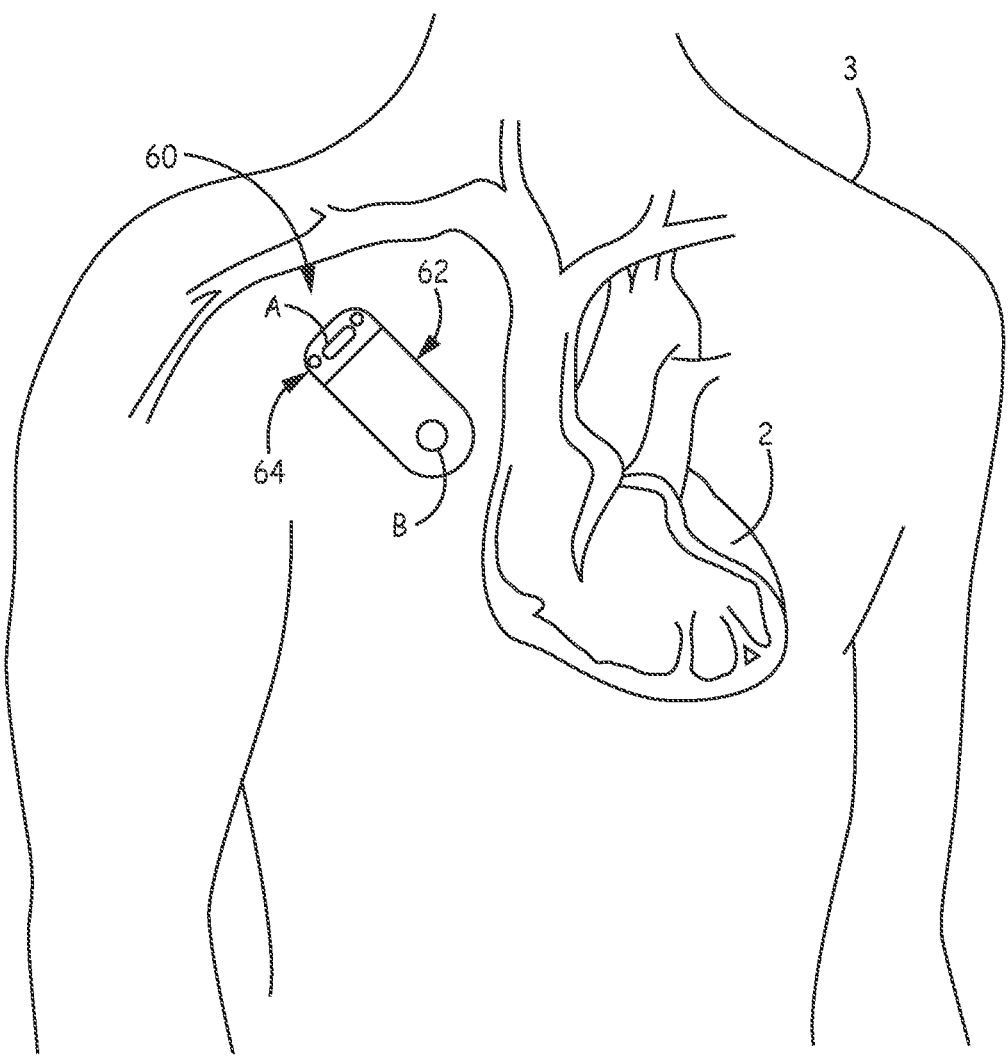
FIG. 1C is a conceptual diagram of yet another IMD system in which techniques disclosed herein may be implemented for detecting atrial tachyarrhythmia.

FIG. 1C is a conceptual diagram of a cardiac monitoring device 60 which may employ aspects of the atrial tachyarrhythmia detection techniques disclosed herein. Monitoring device 60 is shown implanted subcutaneously in the upper thoracic region of a patient's body 3 and displaced from the patient's heart 2. The housing 62 of cardiac monitor 60 (shown enlarged in scale compared to the patient's body 3) includes a non-conductive header module 64 attached to a hermetically sealed housing 62. The housing 62 contains the circuitry of the cardiac monitor 60 and is generally electrically conductive but may be covered in part by an electrically insulating coating. A first, subcutaneous, sense electrode, A, is formed on the surface of the header module 64 and a second, subcutaneous, sense electrode, B, is formed by at least a portion of the housing 62. For example, electrode B may be an exposed portion of housing 62 when housing 62 is coated by an electrically insulating coating. The conductive housing electrode B may be directly connected with the sensing circuitry.

An electrical feedthrough extends through the mating surfaces of the header module 64 and the housing 62 to electrically connect the first sense electrode A with sensing circuitry enclosed within the housing 62. The electrical signals attendant to the depolarization and re-polarization of the heart 2 are referred to as the cardiac electrical signals and are sensed across the sense electrodes A and B and include at least R-waves attendant to the ventricular depolarizations of heart 2. The cardiac monitoring device 60 may be sutured to subcutaneous tissue at a desired orientation of its electrodes A and B to the axis of the heart 8 to detect and record the cardiac electrical signals in a sensing vector A-B for subsequent processing and uplink telemetry transmission to an external device 40 (shown in FIG. 1A).

In one embodiment, the spacing between electrodes A and B may range from 60 mm to 25 mm. In other embodiments, the electrode spacing may range from 55 mm to 30 mm, or from 55 mm to 35 mm. The volume of the implantable cardiac monitoring device 60 may be three cubic centimeters or less, 1.5 cubic centimeters or less or any volume between three and 1.5 cubic centimeters. The length of cardiac monitoring device 60 may range from 30 to 70 mm, 40 to 60 mm or 45 to 60 mm and may be any length between 30 and 70 mm. The width of a major surface such a cardiac monitoring device 60 may range from 3 to 10 mm and may be any thickness between 3 and 10 mm. The thickness of cardiac monitoring device 60 may range from 2 to 9 mm or 2 to 5 mm and may be any thickness between 2 and 9 mm.

The sensing circuitry included in housing 62 is configured to detect the R-waves for monitoring for atrial tachyarrhythmia according to the techniques disclosed herein. Such sensing circuitry may include a pre-filter and amplifier, a rectifier, a sense amplifier, an analog-to-digital filter, a comparator and/or other components configured to receive cardiac electrical signals. Aspects of a cardiac monitoring device of the type that may employ atrial arrhythmia detection techniques disclosed herein are generally disclosed in U.S. Publication No. 2015/0088216 (Gordon, et al.) and U.S. Pat. No. 7,027,858 (Cao, et al.), both incorporated herein by reference in its entirety.

In general, the hermetically sealed housing 62 includes a lithium battery or other power source, a processor and memory or other control circuitry that controls device operations and records arrhythmic cardiac electrical signal episode data in memory registers, and a telemetry transceiver antenna and circuit that receives downlink telemetry commands from and transmits stored data in a telemetry uplink to the external device 40. The circuitry and memory may be implemented in discrete logic or a micro-computer based system with A/D conversion of sampled cardiac electrical signal amplitude values. One implantable cardiac monitor that can be modified in accordance with the presently disclosed techniques is described in U.S. Pat. No. 6,412,490 (Lee et al.), incorporated herein by reference in its entirety, as well as the cardiac monitors disclosed in any of the above-incorporated references.

Figure 2:
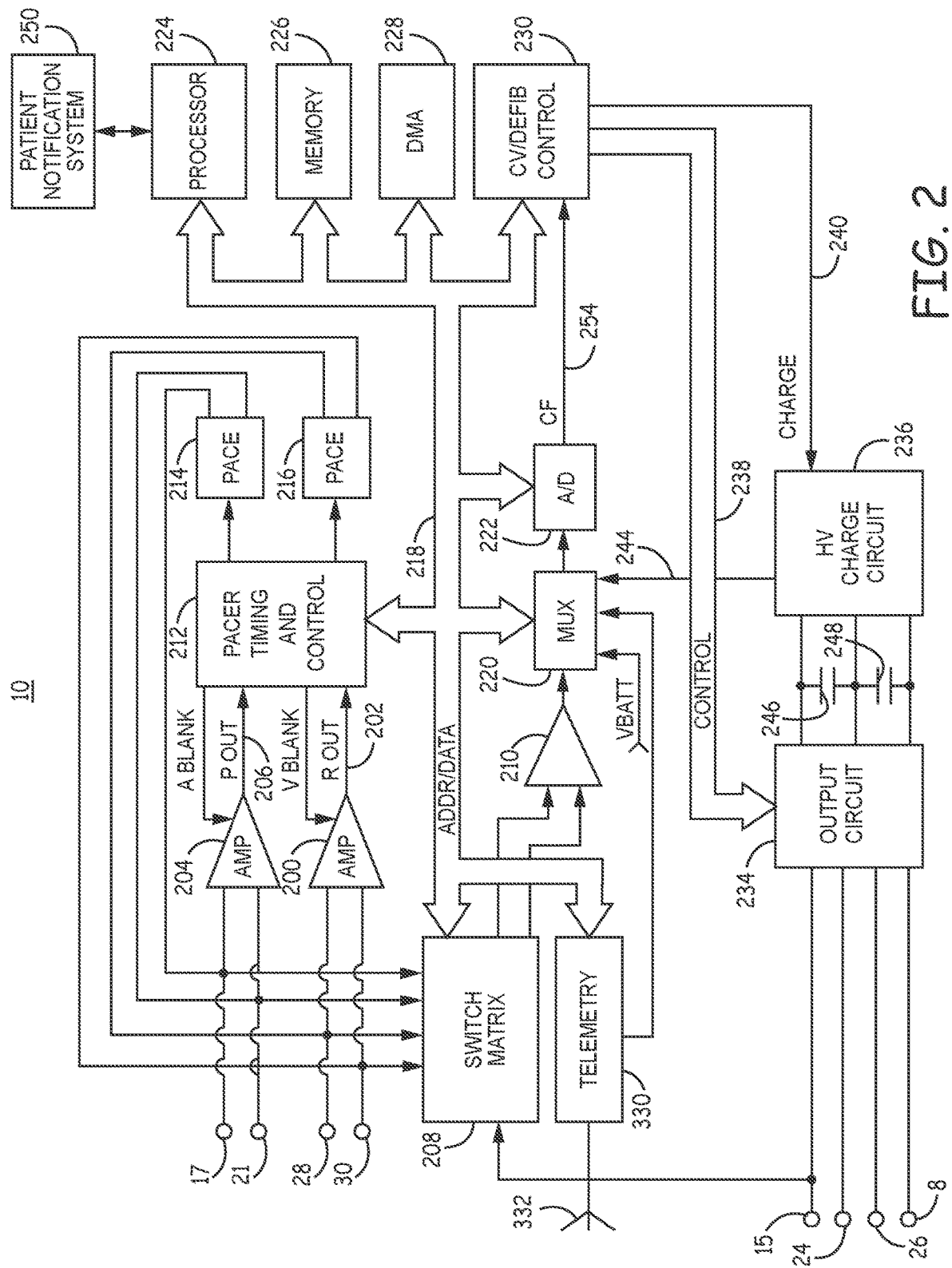
FIG. 2 is a functional schematic diagram of the implantable cardioverter defibrillator (ICD) of FIG. 1.

FIG. 2 is a functional schematic diagram of an ICD, such as ICD 10 of FIG. 1. This diagram should be taken as illustrative of the type of device with which the techniques disclosed herein may be embodied and not as limiting. The example shown in FIG. 2 is a processor-controlled device, but the disclosed methods may also be practiced with other types of devices such as those employing dedicated digital circuitry. In other words, processor 224 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processor 224 may include multiple components, such as any combination of one or more microprocessors, one or more DSPs, one or more ASICs, or one or more FPGAs, as well as other discrete or integrated logic circuitry, and/or analog circuitry.

With regard to the electrode system illustrated in FIG. 1A, ICD 10 is provided with a number of connection terminals for achieving electrical connection to the leads 6, 11, and 16 and their respective electrodes. Housing 15 may be used as an indifferent electrode during unipolar stimulation or sensing. Electrodes 24, 26 and 8 may be selectively coupled to the high voltage output circuit 234 to facilitate the delivery of high energy shocking pulses to the heart using one or more of the coil electrodes 8, 24 and 26 and optionally the housing 15.

RA tip electrode 17 and RA ring electrode 21 may be coupled to atrial sense amplifier 204 for sensing atrial signals such as P-waves. RV tip electrode 28 and the RV ring electrode 30 may be coupled to a ventricular sense amplifier 200 for sensing ventricular signals. The atrial sense amplifier 204 and the ventricular sense amplifier 200 may take the form of automatic gain controlled amplifiers with adjustable sensitivity. ICD 10 and, more specifically, processor 224 may automatically adjust the sensitivity of atrial sense amplifier 204, ventricular sense amplifier 200 or both in response to detection of oversensing in order to reduce the likelihood of oversensing of cardiac events and/or non-cardiac noise.

Atrial sense amplifier 204 and ventricular sense amplifier 200 may receive timing information from pacer timing and control circuitry 212. For example, atrial sense amplifier 204 and ventricular sense amplifier 200 may receive blanking period input, e.g., A_BLANK and V_BLANK, respectively, which indicates the amount of time the amplifiers are "turned off" in order to prevent saturation due to an applied pacing pulse or defibrillation shock. The general operation of the ventricular sense amplifier 200 and the atrial sense amplifier 204 may correspond to that disclosed in U.S. Pat. No. 5,117,824 (Keimel, et al.), incorporated herein by reference in its entirety. Whenever a signal received by atrial sense amplifier 204 exceeds an atrial sensitivity, a signal is generated on the P-out signal line 206. Whenever a signal received by the ventricular sense amplifier 200 exceeds a ventricular sensitivity, a signal is generated on the R-out signal line 202. As described below, a signal on the R-out signal line 202, which may be referred to as a ventricular sense event (Vs event) signal, may be received by processor 224 and used for determining RRI differences.

Switch matrix 208 is used to select which of the available electrodes 8, 17, 21, 24, 26, 28 and 30 are coupled to a wide band amplifier 210 for use in digital signal analysis. Selection of the electrodes is controlled by the processor 224 via data/address bus 218. The selected electrode configuration may be varied as desired for the various sensing, pacing, cardioversion and defibrillation functions of the ICD 10. For example, while RV electrodes 28 and 30 are shown coupled to sense amplifier 200 and pace output circuit 216 suggesting dedicated pace/sense electrodes and coil electrodes 24 and 26 are shown coupled to HV output circuit 234 suggesting dedicated CV/DV shock electrodes, it is recognized that switching circuitry included in switch matrix 208 may be used to select any of the available electrodes in a sensing electrode vector, a pacing electrode vector, or a CV/DF shock vector as indicated previously.

Signals from the electrodes selected for coupling to bandpass amplifier 210 are provided to multiplexer 220, and thereafter converted to multi-bit digital signals by A/D converter 222, for storage in memory 226 under control of direct memory access circuit 228 via data/address bus 218. Processor 224 may employ digital signal analysis techniques to characterize the digitized signals stored in memory 226 to recognize and classify the patient's heart rhythm employing any of numerous signal processing methodologies for analyzing cardiac signals and cardiac event waveforms, e.g., P-waves and R-waves. One tachyarrhythmia detection system is described in U.S. Pat. No. 5,545,186 (Olson et al.), incorporated herein by reference in its entirety.

It is to be understood that the circuitry shown in FIG. 2 may be modified according to the particular device requirements. For example, the single chamber ICD 10' of FIG. 1B may include the ventricular sense amplifier 200 and ventricular pace output circuit 216 and terminals for electrically coupling to electrodes 24, 26, 28 and 30, while atrial sense amplifier 204, atrial pace output circuit 214 and terminals for electrically coupling to electrodes 8, 17 and 21 may be omitted and/or coupled to other electrodes. For example, sense amplifier 204 and/or pace output circuit 214 may be coupled to electrodes 24, 26, and/or housing electrode 15.

Upon detection of an arrhythmia, an episode of cardiac signal data, along with sensed intervals and corresponding annotations of sensed events, may be stored in memory 226. The cardiac electrical signals sensed from programmed sensing electrode pairs may be stored as EGM signals. Typically, a near-field sensing electrode pair includes a tip electrode and a ring electrode located in the atrium or the ventricle, such as RA electrodes 17 and 21 or RA electrodes 28 and 30. A far-field sensing electrode pair includes electrodes spaced further apart such as any of: the defibrillation coil electrodes 8, 24 or 26 with housing 15; a tip electrode 17 or 28 with housing 15; a tip electrode 17 or 28 with a defibrillation coil electrode 8, 24 or 26; or atrial tip electrode 17 with ventricular ring electrode 30. The use of near-field and far-field EGM sensing of arrhythmia episodes is described in U.S. Pat. No. 5,193,535 (Bardy), incorporated herein by reference in its entirety. Annotation of sensed events, which may be displayed and stored with EGM data, is described in U.S. Pat. No. 4,374,382 (Markowitz), incorporated herein by reference in its entirety.

FIG. 2 may suggest only two sensing channels, an atrial sensing channel including amplifier 204 and a ventricular sensing channel including amplifier 200, in ICD 10, however it is recognized that the techniques disclosed herein may be applied to one or more cardiac electrical signals acquired using any combination of the available electrodes. In some examples, a first cardiac electrical signal is acquired between the ICD housing 15 and RV coil electrode 24, a second cardiac electrical signal is acquired between the RV coil electrode 24 and the SV coil electrode 26, and third cardiac electrical signal is acquired between the RV tip electrode 28 and the RV ring electrode 30. All three signals may be collected and used by processor 224 for analyzing R-waves and RRIs and detecting atrial and/or ventricular arrhythmias. As discussed below in conjunction with FIG. 11, at least two cardiac signals may be stored in memory 226 in the example of FIG. 2, when a tachyarrhythmia episode is detected for later transmission by telemetry circuit 330. When atrial tachyarrhythmia is detected, with or without simultaneous detection of ventricular tachyarrhythmia, the two signals may be stored having two different gain settings to provide two different signals for display on external device 40. One signal displayed at a higher gain may result in R-wave clipping but enables relatively small amplitude P-waves to be more readily observed, which enables any relationship between the detected atrial and ventricular tachyarrhythmia (if present) to be observed by a clinician through comparison of the two different signals. When ventricular tachyarrhythmia is detected without atrial tachyarrhythmia detection, two signals may be stored both having a gain setting that avoids clipping of R-waves.

The telemetry circuit 330 includes a transceiver for receiving downlink telemetry from and sending uplink telemetry to external device 40 using antenna 332. Telemetry circuit 330 provides bi-directional telemetric communication with an external device 40 as described above.

ICD 10 may receive programmable operating parameters and algorithms via telemetry circuit 330 for storage in memory 226 or other memory. For example, memory 226 may be any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 226 may be accessed by processor 224 for controlling ICD functions. For example, cardiac rhythm detection parameters and therapy control parameters used by ICD 10 may be programmed via telemetry circuit 330. Thus, memory 226 of IMD 10 may store program instructions, which may include one or more program modules, which are executable by processor 224. When executed by processor 224, such program instructions may cause processor 224 and IMD 10 to provide the functionality ascribed to them herein. The program instructions may be embodied in software, firmware and/or RAMware.

Data stored or acquired by ICD 10, including physiological signals or associated data derived therefrom, results of device diagnostics, and histories of detected arrhythmia episodes and delivered therapies, may be retrieved from ICD 10 by the external device 40 following an interrogation command received by telemetry circuit 330. Data to be unlinked to the external device and control signals for the telemetry circuit 330 are provided by processor 224 via address/data bus 218. Received telemetry is provided to processor 224 via multiplexer 220. Numerous types of telemetry systems known for use in implantable medical devices may be implemented in ICD 10.

Other circuitry shown in FIG. 2 is illustrative of therapy delivery circuitry that may be included in an ICD or other implantable medical device employing the atrial arrhythmia detection technique disclosed herein when the device is configured for providing cardiac pacing, cardioversion and defibrillation therapies. For example, the pacer timing and control circuitry 212 may include programmable digital counters which control the basic time intervals associated with various single, dual or multi-chamber pacing modes or anti-tachycardia pacing therapies delivered in the atria or ventricles. Pacer timing and control circuitry 212 also sets the amplitude, pulse width, polarity or other characteristics of the cardiac pacing pulses under the control of processor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pace output circuit 214 and ventricular pace output circuit 216. The pace output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by processor 224 via data/address bus 218. The value of the count present in the escape interval counters when reset by sensed R-waves or P-waves can be used to measure R-R intervals and P-P intervals for detecting the occurrence of a variety of arrhythmias. Processor 224 may also track the number of pacing pulses delivered, particularly the number of ventricular pacing pulses delivered, during predetermined time periods as a factor used in classifying the cardiac electrical signal during the time period.

The processor 224 includes associated read-only memory (ROM) in which stored programs controlling the operation of the processor 224 reside. A portion of the random access memory (RAM) 226 may be configured as a number of recirculating buffers capable of holding a series of measured intervals for analysis by the processor 224 for predicting or diagnosing an arrhythmia.

In response to the detection of tachycardia, anti-tachycardia pacing therapy can be delivered by loading a regimen from processor 224 into the pacer timing and control circuitry 212 according to the type of tachycardia detected. In the event that higher voltage cardioversion or defibrillation pulses are required, processor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by processor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

When ICD 10 is coupled to a RA lead 11 as shown in FIG. 1A, atrial electrical stimulation therapies may be delivered in response to detecting atrial tachyarrhythmia using the techniques disclosed herein. In some examples, atrial pacing and/or an atrial cardioversion/defibrillation shock may be delivered to terminate a sustained atrial tachyarrhythmia.

In some examples, the ICD 10 may be equipped with a patient notification system 250. Any patient notification method known for use in implantable medical devices may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 (Greeninger et al.), incorporated herein by reference in its entirety. In some examples, ICD 10 provides a response to an atrial tachyarrhythmia detection by generating a patient notification via system 250 and/or a clinician notification using telemetry circuit 330. An atrial tachyarrhythmia response provided by ICD 10 may include determining an AF burden as the total combined duration of all detected AF episodes during a predetermined monitoring time interval, e.g., 24 hours, and generating a patient notification and/or clinician notification when the AF burden exceeds a threshold.

Figure 3A:
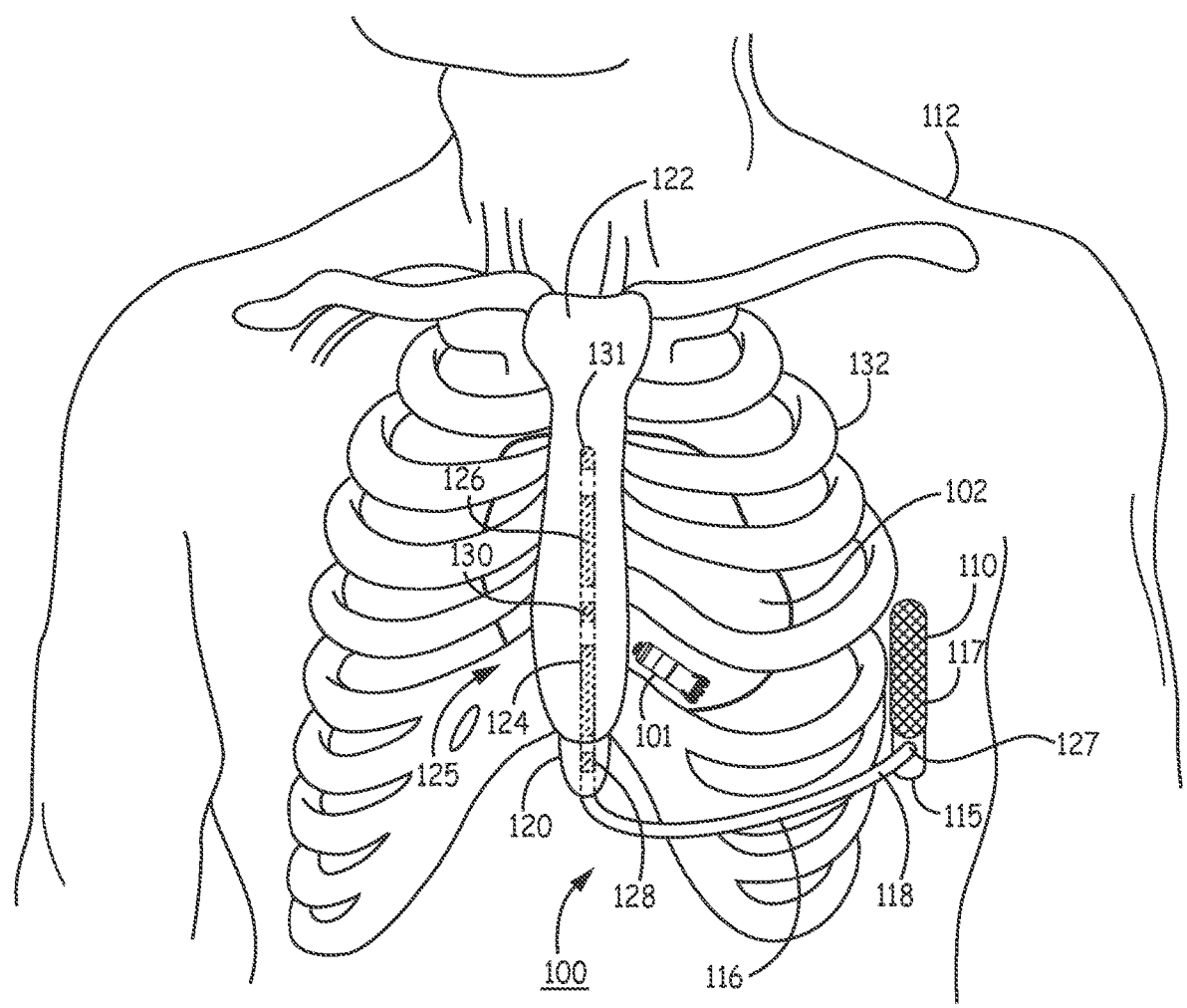
FIGS. 3A and 3B are conceptual diagrams of an alternative ICD system that may be configured to detect atrial tachyarrhythmia according to the techniques disclosed herein.
Figure 3B:
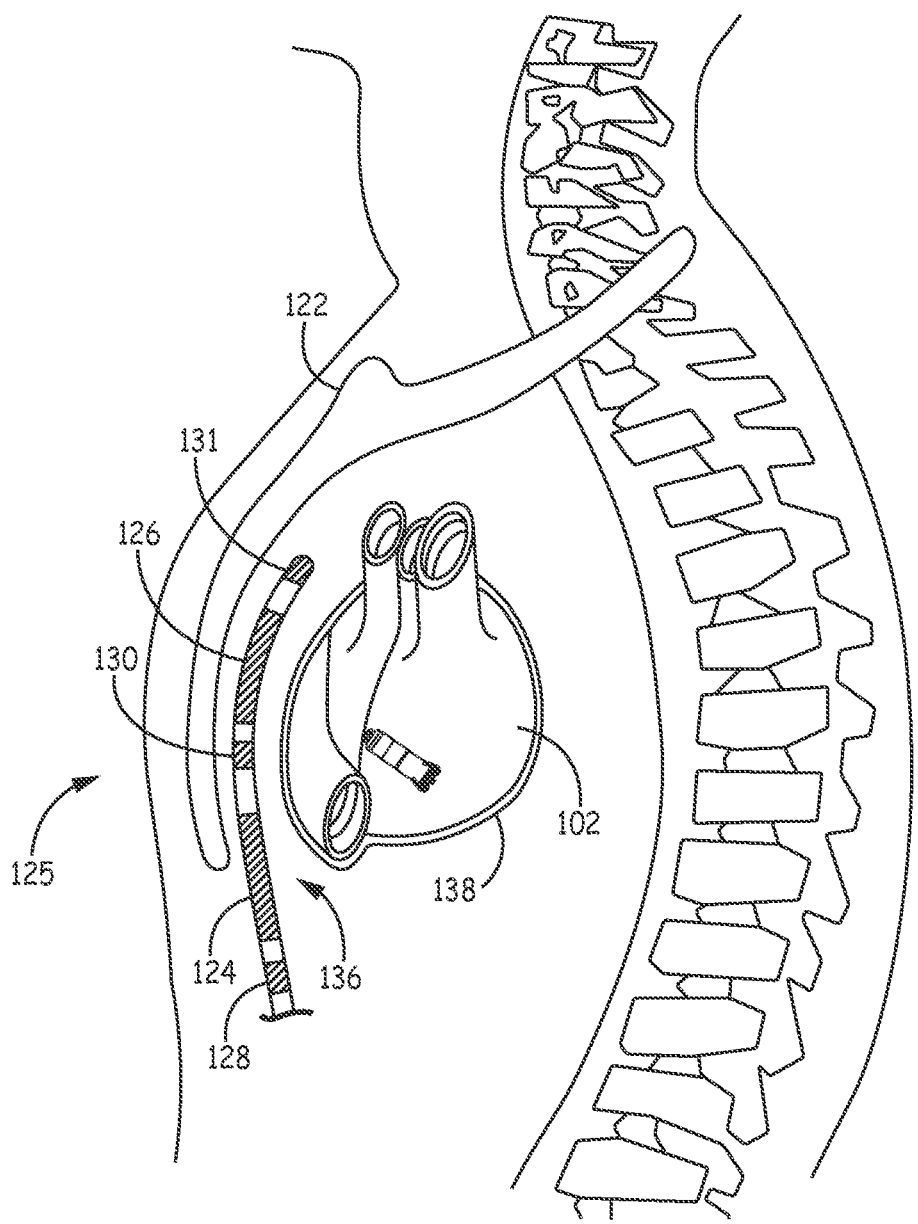

FIGS. 3A and 3B are conceptual diagrams of an alternative ICD system 100 that may be configured to detect AF according to the techniques disclosed herein. FIG. 3A is a front view of an extra-cardiovascular ICD system 100 implanted within patient 112. FIG. 3B is a side view of ICD system 100 implanted within patient 112. ICD system 100 includes an ICD 110 connected to an extra-cardiovascular electrical stimulation and sensing lead 116. ICD system 100 may further include an intracardiac pacemaker 101 configured to deliver pacing pulses to a ventricular or atrial chamber.

ICD 110 includes a housing 115 that forms a hermetic seal that protects internal components of ICD 110. Internal device components may include circuitry shown in FIG. 2, such as sense amplifier(s), A/D converter, pacing output circuitry, high voltage output circuitry and a processor and memory and/or other control circuitry. The housing 115 of ICD 110 may be formed of a conductive material, such as titanium or titanium alloy. The housing 115 may function as a housing electrode (sometimes referred to as a can electrode). In examples described herein, housing 115 may be used as an active can electrode for use in delivering cardioversion/defibrillation (CV/DF) shocks or other high voltage pulses delivered by HV charge circuit 236 (FIG. 2). In other examples, housing 115 may be available for use in sensing cardiac signals or for delivering unipolar, low voltage cardiac pacing pulses by a pacer output circuit in conjunction with lead-based cathode electrodes. In other instances, the housing 115 of ICD 110 may include multiple electrodes on an outer portion of the housing. The outer portion(s) of the housing 115 functioning as an electrode(s) may be coated with a material, such as titanium nitride.

ICD 110 includes a connector assembly 117 (also referred to as a connector block or header) that includes electrical feedthroughs crossing housing 115 to provide electrical connections between conductors extending within the lead body 118 of lead 116 and electronic components included within the housing 115 of ICD 110. As described above in conjunction with FIG. 2, housing 115 may house one or more processors, memories, telemetry transceivers, sensing circuitry such as sense amplifiers and analog-to digital converters, therapy delivery circuitry such as pacer timing and control, CV/DF control, pace output and HV output circuits and associated charging circuits, a switch matrix, a data bus, one or more batteries or other power sources and other components for sensing cardiac electrical signals, detecting a heart rhythm, and controlling and delivering electrical stimulation pulses to treat an abnormal heart rhythm.

Lead 116 includes an elongated lead body 118 having a proximal end 127 that includes a lead connector (not shown) configured to be connected to ICD connector assembly 117 and a distal portion 125 that includes one or more electrodes. In the example illustrated in FIGS. 3A and 3B, the distal portion 125 of lead 116 includes defibrillation electrodes 124 and 126 and pace/sense electrodes 128, 130 and 131. In some cases, defibrillation electrodes 124 and 126 may together form a defibrillation electrode in that they may be configured to be activated concurrently. Alternatively, defibrillation electrodes 124 and 126 may form separate defibrillation electrodes in which case each of the electrodes 124 and 126 may be activated independently. In some instances, defibrillation electrodes 124 and 126 are coupled to electrically isolated conductors, and ICD 110 may include switching mechanisms to allow electrodes 124 and 126 to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 115 as an active electrode).

Electrodes 124 and 126 (and in some examples housing 115) are referred to herein as defibrillation electrodes because they are utilized, individually or collectively, for delivering high voltage stimulation therapy (e.g., cardioversion or defibrillation shocks). Electrodes 124 and 126 may be elongated coil electrodes and generally have a relatively high surface area for delivering high voltage electrical stimulation pulses compared to low voltage pacing and sensing electrodes 28, 30 and 31. However, electrodes 124 and 126 and housing 115 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 124 and 126 for use in only high voltage cardioversion/defibrillation shock therapy applications. Electrodes 124 and 126 may be used in a pacing electrode vector for delivering extra-cardiovascular pacing pulses such as ATP pulses, post-shock pacing or other pacing therapies and/or in a sensing vector used to sense cardiac electrical signals for detecting atrial and ventricular arrhythmias, referred to generally as "cardiac events", including AF, VT and VF.

Electrodes 128, 130 and 131 are relatively smaller surface area electrodes for delivering low voltage pacing pulses and for sensing cardiac electrical signals. Electrodes 128, 130 and 131 are referred to as pace/sense electrodes because they are generally configured for use in low voltage applications, e.g., used as either a cathode or anode for delivery of pacing pulses and/or sensing of cardiac electrical signals. Electrodes 124, 126, 128, 130 and/or 131 may be used to acquire cardiac electrical signals used for AF detection according to the techniques disclosed herein.

Lead 16 extends subcutaneously or submuscularly over the ribcage 132 medially from the connector assembly 127 of ICD 110 toward a center of the torso of patient 112, e.g., toward xiphoid process 120 of patient 112. At a location near xiphoid process 120, lead 116 bends or turns and extends superiorly within anterior mediastinum 136 in a substernal position. Lead 116 of system 100 is implanted at least partially underneath sternum 122 of patient 112.

Anterior mediastinum 136 may be viewed as being bounded laterally by pleurae, posteriorly by pericardium 138, and anteriorly by sternum 122. In some instances, the anterior wall of anterior mediastinum 136 may also be formed by the transversus thoracis muscle and one or more costal cartilages. Anterior mediastinum 136 includes a quantity of loose connective tissue (such as areolar tissue), adipose tissue, some lymph vessels, lymph glands, substernal musculature, small side branches of the internal thoracic artery or vein, and the thymus gland. In one example, the distal portion 125 of lead 116 extends along the posterior side of sternum 122 substantially within the loose connective tissue and/or substernal musculature of anterior mediastinum 136.

A lead implanted such that the distal portion 125 is substantially within anterior mediastinum 136 may be referred to as a "substernal lead." In the example illustrated in FIGS. 3A and 3B, lead 116 extends substantially centered under sternum 122. In other instances, however, lead 116 may be implanted such that it extends in a position that is offset laterally from the center of sternum 122. In some instances, lead 116 may extend laterally such that distal portion 125 of lead 116 is underneath/below the ribcage 132 in addition to or instead of sternum 122. In other examples, the distal portion 125 of lead 116 may be implanted in other extra-cardiovascular, intra-thoracic locations, including the pleural cavity or around the perimeter of and adjacent to but typically not within the pericardium 138 of heart 102.

In other examples, lead 116 may remain outside the thoracic cavity and extend subcutaneously or submuscularly over the ribcage 132 and/or sternum 122. The path of lead 116 may depend on the location of ICD 110, the arrangement and position of electrodes carried by the lead distal portion 125, and/or other factors.

Electrical conductors (not illustrated) extend through one or more lumens of the elongated lead body 118 of lead 116 from the lead connector at the proximal lead end 127 to electrodes 124, 126, 128, 130 and 131 located along the distal portion 125 of the lead body 118. The lead body 118 of lead 116 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 118 are each electrically coupled with respective defibrillation electrodes 124 and 126 and pace/sense electrodes 128, 130 and 131. Each of pacing and sensing electrodes 128, 130 and 131 are coupled to respective electrical conductors, which may be separate respective conductors within the lead body. The respective conductors electrically couple the electrodes 124, 126, 128, 130 and 131 to circuitry, such as a switch matrix or other switching circuitry for selection and coupling to a sense amplifier or other cardiac event detection circuitry and/or to a therapy output circuit, e.g., a pacing output circuit or a HV output circuit for delivering CV/DF shock pulses. Connections between electrode conductors and ICD circuitry is made via connections in the connector assembly 117, including associated electrical feedthroughs crossing housing 115. The electrical conductors transmit therapy from an output circuit within ICD 110 to one or more of defibrillation electrodes 124 and 126 and/or pace/sense electrodes 128, 130 and 131 and transmit sensed electrical signals from one or more of defibrillation electrodes 124 and 126 and/or pace/sense electrodes 128, 130 and 131 to the sensing circuitry within ICD 110.

ICD 110 may obtain electrical signals corresponding to electrical activity of heart 102 via a combination of sensing vectors that include combinations of electrodes 128, 130, and/or 131. In some examples, housing 115 of ICD 110 is used in combination with one or more of electrodes 128, 130 and/or 131 in a sensing electrode vector. ICD 110 may even obtain cardiac electrical signals using a sensing vector that includes one or both defibrillation electrodes 124 and/or 126, e.g., between electrodes 124 and 126 or one of electrodes 124 or 126 in combination with one or more of electrodes 128, 130, 131, and/or the housing 115.

ICD 110 analyzes the cardiac electrical signals received from one or more of the sensing vectors to monitor for abnormal rhythms, such as AF, VT and VF. ICD 110 generates and delivers electrical stimulation therapy in response to detecting a ventricular tachyarrhythmia (e.g., VT or VF). ICD 110 may deliver ATP in response to VT detection, and in some cases may deliver ATP prior to a CV/DF shock or during high voltage capacitor charging in an attempt to avert the need for delivering a CV/DF shock. ICD 110 may deliver a CV/DF shock pulse when VF is detected or when VT is not terminated by ATP.

In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28, 30 and/or 31 may be located elsewhere along the length of lead 16. For example, lead 16 may include a single pace/sense electrode 30 between defibrillation electrodes 24 and 26 and no pace/sense electrode distal to defibrillation electrode 26 or proximal defibrillation electrode 24. Various example configurations of extra-cardiovascular leads and electrodes and dimensions that may be implemented in conjunction with the AF detection techniques disclosed herein are described in commonly-assigned U.S. patent application Ser. No. 14/519,436, U.S. patent application Ser. No. 14/695,255 and provisionally-filed U.S. Pat. Application No. 62/089,417, all of which are incorporated herein by reference in their entirety.

ICD 110 is shown implanted subcutaneously on the left side of patient 112 along the ribcage 132. ICD 110 may, in some instances, be implanted between the left posterior axillary line and the left anterior axillary line of patient 112. ICD 110 may, however, be implanted at other subcutaneous or submuscular locations in patient 112. For example, ICD 110 may be implanted in a subcutaneous pocket in the pectoral region. In this case, lead 116 may extend subcutaneously or submuscularly from ICD 110 toward the manubrium of sternum 122 and bend or turn and extend inferior from the manubrium to the desired location subcutaneously or submuscularly. In yet another example, ICD 110 may be placed abdominally.

In some patients, an intracardiac pacemaker 101 may be present in the right ventricle, right atrium or along the left ventricle. Pacemaker 101 may be configured to deliver pacing pulses in the absence of sensed intrinsic heart beats, in response to detecting VT, or according to other pacing therapy algorithms. For example, pacemaker 101 may be implanted in the right ventricle of the patient for providing single chamber ventricular pacing. The techniques disclosed herein for classifying a cardiac signal may be utilized in the presence of ventricular pacing delivered by ICD 110 and/or by an intracardiac pacemaker such as pacemaker 101. Pacemaker 101 may generally correspond to the intracardiac pacemaker disclosed in U.S. Pat. No. 8,923,963 (Bonner, et al.), incorporated herein by reference in its entirety. ICD 110 may be configured to detect pacing pulses delivered by pacemaker 101. The frequency of pacing pulses delivered by pacemaker 101 may be a factor determined in classifying a cardiac electrical signal time period for AF detection purposes.

Pacemaker 101 may have limited processing power and therapy delivery capacity compared to ICD 110 such that the advanced cardiac rhythm detection techniques disclosed herein may be implemented in ICD 110 rather than in pacemaker 101. As such, the methods disclosed herein are described in conjunction with ICD 10, 10' or ICD 110 or cardiac monitoring device 60. These techniques, however, are not to be considered limited to being implemented in an ICD or subcutaneous or external cardiac monitor. Aspects of the AF detection techniques disclosed herein may be implemented in pacemaker 101, all or in part.

Figure 4:
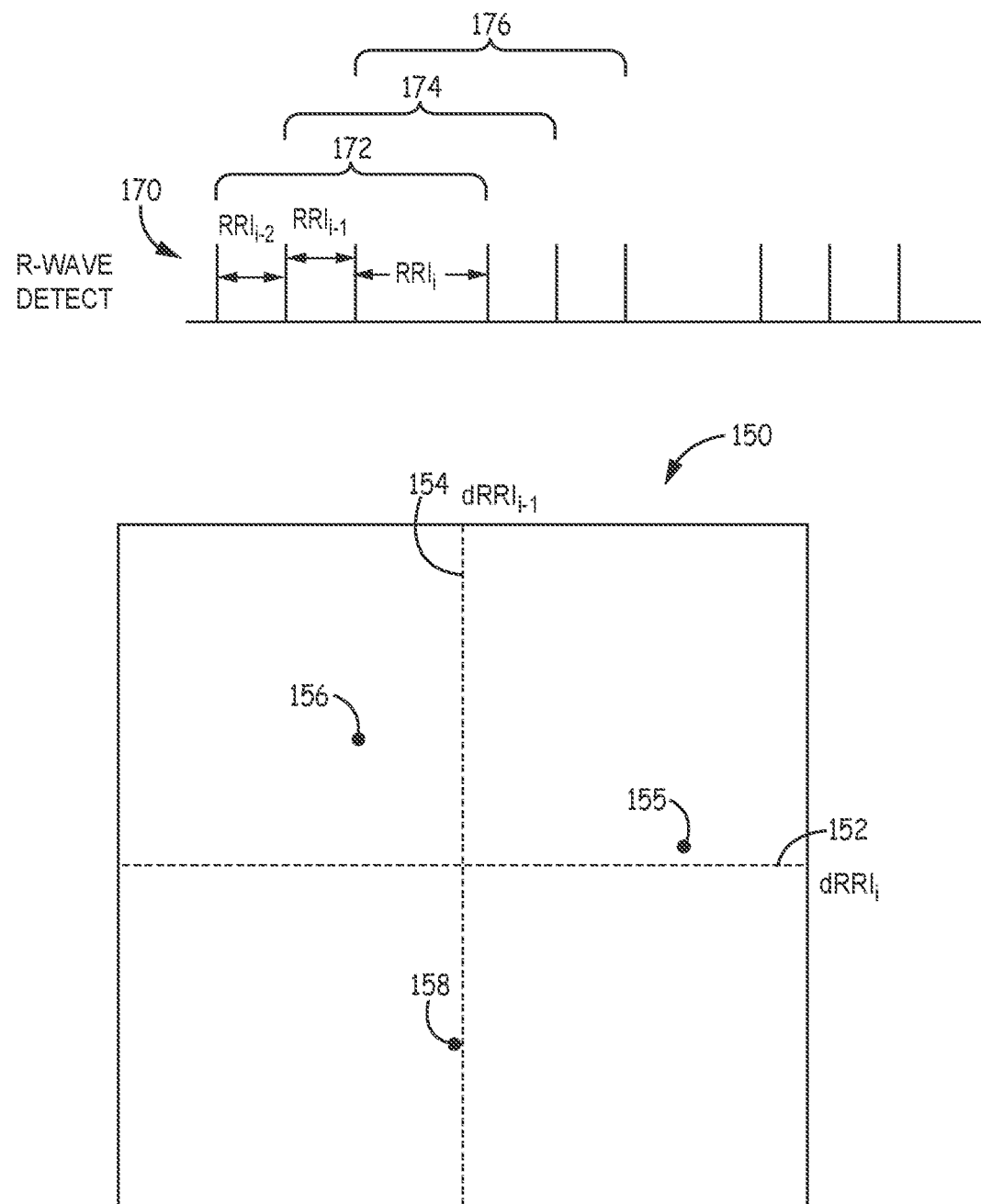
FIG. 4 is a schematic diagram of methods used for detecting cardiac events by any of the ICDs of FIGS. 1A, 1B and 2 or the monitoring device of FIG. 1C according to one example.

FIG. 4 is a schematic diagram of methods used for detecting cardiac events by a medical device, such as ICD 10, ICD 10', cardiac monitoring device 60, or ICD 110, according to one example. Single chamber devices have been designed to detect AF using a ventricular EGM signal. Illustrative methods and devices for detecting AF using a ventricular EGM signal are generally described in commonly assigned U.S. patent application Ser. Nos. 14/520, 798, 14/520,938 and 14/520,847 (Cao et al.), all of which are incorporated herein by reference in their entirety. R-waves attendant to the ventricular depolarization are sensed from the ventricular EGM signal and used to determine RRIs, i.e., intervals between successive R-waves. Successive RRI differences are determined by subtracting an RRI from an immediately preceding RRI. An analysis of a Lorenz plot of the successive RRI differences may reveal an RRI variability pattern that is typical of AF.

Methods for detecting atrial arrhythmias based on the irregularity of ventricular cycles determined from RRI differences that exhibit discriminatory signatures when plotted in a Lorenz scatter plot, such as the plot shown in FIG. 4, are generally disclosed by Ritscher et al. in U.S. Pat. No. 7,031,765, incorporated herein by reference in its entirety. Other methods are generally disclosed by Sarkar, et al. in U.S. Pat. No. 7,623,911 and in U.S. Pat. No. 7,537,569 and by Houben in U.S. Pat. No. 7,627,368, all of which patents are also incorporated herein by reference in their entirety.

In the following description, AF detection techniques are described with reference to the circuitry of FIG. 2 and ICD 10 of FIG. 1A. It is to be understood, however, that the methods and techniques of the descriptions that follow may be implemented in ICD 10' of FIG. 1B, ICD 110 of FIGS. 3A and 3B or a cardiac monitoring device such as the device of FIG. 1C, all of which devices may include a processor, memory and sensing circuitry, as generally described in conjunction with FIG. 2, for performing these AF detection techniques.

In order to determine whether AF is occurring, the processor 224 (FIG. 2) may determine differences between RRIs based on sensed R-waves (e.g., R OUT signal line 202 in FIG. 2). Processor 224 may make the decision as to whether an AF event is occurring based at least in part on the resulting pattern or signature of RRI differences. As described below, when the resulting signature of RRI differences acquired over a predetermined time period indicates AF is occurring, the cardiac signal time period is classified as AF. AF is detected when a required number of time periods are classified as AF. Techniques disclosed herein may be utilized as part of an overall tachyarrhythmia detection and discrimination algorithm implemented in ICD 10 or the other devices described above or in other implantable or external cardiac devices, such as an intracardiac pacemaker, a leadless pacemaker or an external device.

The concept of using a signature of RRI differences for detecting AF is illustrated by the generation of a Lorenz scatter plot as shown in FIG. 4. Processor 224 determines the differences between consecutive pairs of RR-intervals ($\delta RRs$) which can be plotted for a time series of RRIs. The Lorenz plot 150 is a Cartesian coordinate system defined by $\delta RR_i$ along the x-axis 152 and $\delta RR_{i-1}$ along the y-axis 154. As such, each plotted point in a Lorenz plot is defined by an x-coordinate equaling $\delta RR_i$ and a y-coordinate equaling $\delta RR_{i-1}$. $\delta RR_i$ is the difference between the $i^{th}$ RRI and the previous RRI, $RRI_{i-1}$. $\delta RR_{i-1}$ is the difference between $RRI_{i-1}$ and the previous RRI, $RRI_{i-2}$.

As such, each data point plotted on the Lorenz plot 150 represents an RRI pattern relating to three consecutive RRIs: $RRI_i$, $RRI_{i-1}$ and $RRI_{i-2}$, measured between four consecutively sensed R-waves. RRI information is not limited to detection of R-waves and determination of RRIs. The terms RRI and $\delta RR_i$ as used herein refer generally to a measurement of ventricular cycle length (VCL) and the difference between two consecutive VCL measurements, respectively, whether the VCL measurements were derived from a series of sensed R-waves from a cardiac electrical signal or a series of ventricular cycle event detections made from another physiological signal (e.g., a peak pressure determined from a pressure signal). For the sake of illustration, the methods described herein refer to R-wave detections for performing VCL measurements and the determination of ($\delta RR_i$, $\delta RR_{i-1}$) points.

As illustrated in FIG. 4, a series of R-waves 170 (represented by vertical bars) are sensed and in order to plot a point on the Lorenz plot area 150, a ($\delta RR_i$, $\delta RR_{i-1}$) point is determined by determining successive RRIs determined from the sensed R-waves 170. In the example shown, a first series 172 of three consecutive RRIs ($RRI_{i-2}$, $RRI_{i-1}$ and $RRI_i$) provides the first data point 155 on the Lorenz plot area 150. $\delta RR_{i-1}$, which is the difference between $RRI_{i-2}$ and $RRI_{i-1}$ is near 0. $\delta RR_i$, the difference between the and $RRI_i$, is a positive change. Accordingly, a ($\delta RR_i$, $\delta RR_{i-1}$) point 155 having a y-coordinate near 0 and a positive x-coordinate is plotted in the Lorenz plot 150, representing the first series 172 of four sensed R-waves (three RRIs).

The next series 174 of three RRIs provides the next ($\delta RR_i$, $\delta RR_{i-1}$) point 156 having a negative x-coordinate (the last RRI of series 174 being less than the immediately preceding RRI) and a positive y-coordinate (the middle RRI of series 174 being longer than the first RRI of series). This process of plotting ($\delta RR_i$, $\delta RR_{i-1}$) points continues with the three cycle series 176 providing data point 158 and so on.

Figure 5:
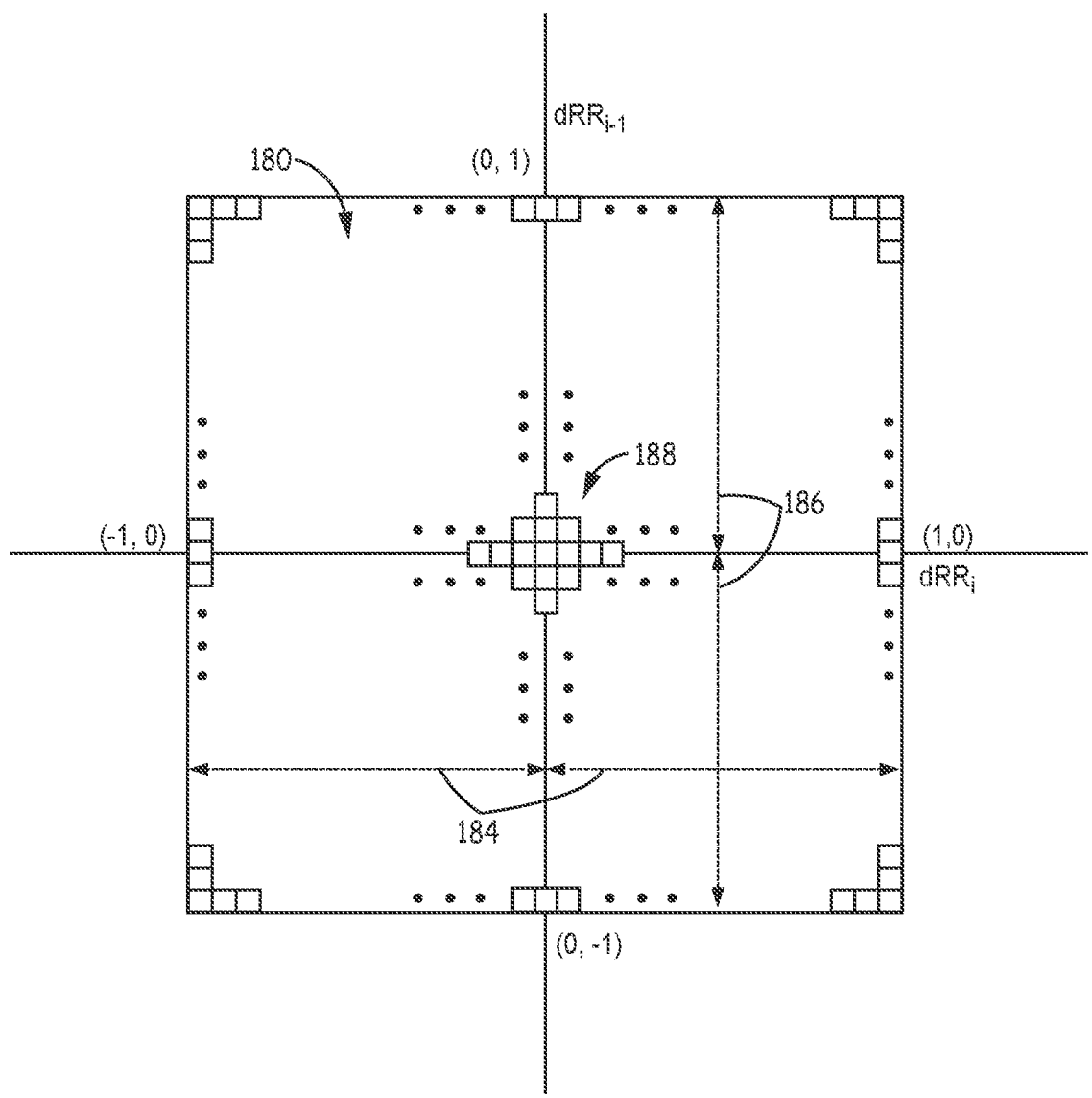
FIG. 5 is a diagram of a two-dimensional histogram representing a Lorenz plot area used in the techniques disclosed herein for detecting atrial tachyarrhythmia.

FIG. 5 is a diagram of a two-dimensional histogram representing a Lorenz plot area 150 used in the techniques disclosed herein for detecting atrial tachyarrhythmia. Generally, the Lorenz plot area 150 shown in FIG. 4 is numerically represented by a two-dimensional histogram 180 having predefined ranges 184 and 186 in both positive and negative directions for the $\delta RR_i$ coordinates (corresponding to x-axis) and $\delta RR_{i-1}$ coordinates (corresponding to y-axis), respectively. The two-dimensional histogram 180 is divided into bins 188 each having a predefined range of $\delta RR_i$ and $\delta RR_{i-1}$ values. In one example, the histogram range might extend from −1200 ms to +1200 ms for both $\delta RR_i$ and $\delta RR_{i-1}$ values, and the histogram range may be divided into bins extending for a range of 7.5 ms in each of the two dimensions resulting in a 160 bin $\lambda$ 160 bin histogram 180. The successive RRI differences determined over a classification time period are used to populate the histogram 180. Each bin stores a count of the number of ($\delta RR_i$, $\delta RR_{i-1}$) data points falling into each respective bin range. The bin counts may then be used by processor 224 in determining RRI variability metrics and patterns for detecting a cardiac rhythm type.

An RRI variability metric is determined from the histogram bin counts. Generally, the more histogram bins that are occupied, or the more sparse the distribution of ($\delta RR_i$, $\delta RR_{i-1}$) points, the more irregular the VCL is during the data acquisition time period. As such, one metric of the RRI variability that can be used for detecting AF, which is associated with highly irregular VCL, may take into account the number of histogram bins that have a count of at least one, which is referred to as an "occupied" bin. In one example, an RRI variability metric for detecting AF, referred to as an AF score, is determined by processor 224 as generally described in the above-incorporated '911 patent. Briefly, the AF score may be defined by the equation:

AF Score=Irregularity Evidence−Origin Count−PAC Evidence wherein Irregularity Evidence is the number of occupied histogram bins outside a Zero Segment 188 defined around the origin of the Lorenz plot area. During normal sinus rhythm or highly organized atrial tachycardia, nearly all points will fall into the Zero Segment 188 because of relatively small, consistent differences between consecutive RRIs. A high number of occupied histogram bins outside the Zero segment 188 is therefore positive evidence for AF.

The Origin Count is the number of points in the Zero Segment 188 defined around the Lorenz plot origin. A high Origin Count indicates regular RRIs, a negative indicator of AF, and is therefore subtracted from the Irregularity Evidence term. In addition, a regular PAC evidence score may be computed as generally described in the above-incorporated '911 patent. The regular PAC evidence score is computed based on a cluster signature pattern of data points that is particularly associated with premature atrial contractions (PACs) that occur at regular coupling intervals and present regular patterns of RRIs, e.g., associated with bigeminy (short-short-long RRIs) or trigeminy (short-short-short-long RRIs). In other embodiments, the AF score and/or other RRI variability score for classifying an atrial rhythm may be determined by processor 224 as described in any of the above-incorporated '765, '316, '911, '569 and '368 patents. Methods for rejecting noise in determining Lorenz plot points and an AF score are generally disclosed in U.S. Pat. No. 8,639,316 (Sarkar, et al.), incorporated herein by reference in its entirety. Methods for adjusting the AF score based on the presence of ectopy may be used in the techniques disclosed herein and are generally disclosed in U.S. Pat. No. 8,977,350 (Sarkar, et al.), incorporated herein by reference in its entirety. Other techniques that may be used in computing an AF score are generally disclosed in U.S. patent application Ser. Nos. 14/695,135, 14/695,156, 14/695,171 and 14/695,111 (Sarkar, et al.), all filed on Apr. 24, 2015 and incorporated herein by reference in their entirety.

The AF score is compared to an AF score threshold for classifying a predetermined time period of a cardiac signal as AF or non-AF based on the RRI analysis. The AF score threshold may be selected and optimized based on historical clinical data of selected patient populations or historical individual patient data, and the optimal AF score threshold setting may vary from patient to patient. In an illustrative example, the AF score may have a possible range of 0 to 100. The AF score threshold may be set between 25 and 75. If the AF score meets or crosses an AF score threshold, the time period over which the RRIs were collected, and thus the cardiac signal occurring within the time period, is classified as an AF time period. The AF score threshold may be adjusted after classifying at least one time period of the cardiac signal as being AF and the adjusted AF score threshold may be used for classifying subsequent time periods, which may lead to an AF detection. The adjusted AF score threshold is less than the initial AF score threshold and may have a value ranging from 19 to 57 in the example given above where the maximum AF score is 100 and the initial AF score threshold is at least 26 and not more than 75. Thus, the adjusted AF score threshold may be between 65-85% of the initial AF score threshold and, in some instances between 70-75% of the initial AF score.

An AF detection is made when a threshold number of time periods are classified as AF. In one example, a single n-second or n-minute time period classified as AF based on the AF score meeting the AF score threshold may result in an AF detection. In other examples, a higher number of time periods may be required to be classified as being AF before detecting the heart rhythm as AF.

The processor 224 provides a response to the AF detection, which may include withholding, adjusting or delivering a therapy (e.g., withholding ATP or shock therapy for treating a ventricular tachyarrhythmia or delivering an atrial anti-tachyarrhythmia therapy if available), storing cardiac signal data that can be later retrieved by a clinician using external device 40, triggering patient notification system 250, transmitting data via telemetry circuit 330 to alert a clinician, and/or triggering other signal acquisition or analysis.

The RRI analysis may continue to be performed by processor 224 after an AF detection is made to fill the histogram during the next n-second detection time period. After each detection time period, the AF score may be re-determined and the histogram bins are re-initialized to zero for the next detection time period. The new AF score (or other RRI variability metrics) determined at the end of each detection time period may be used to determine if the AF episode is sustained or terminated after the initial AF detection is made.

Figure 6:
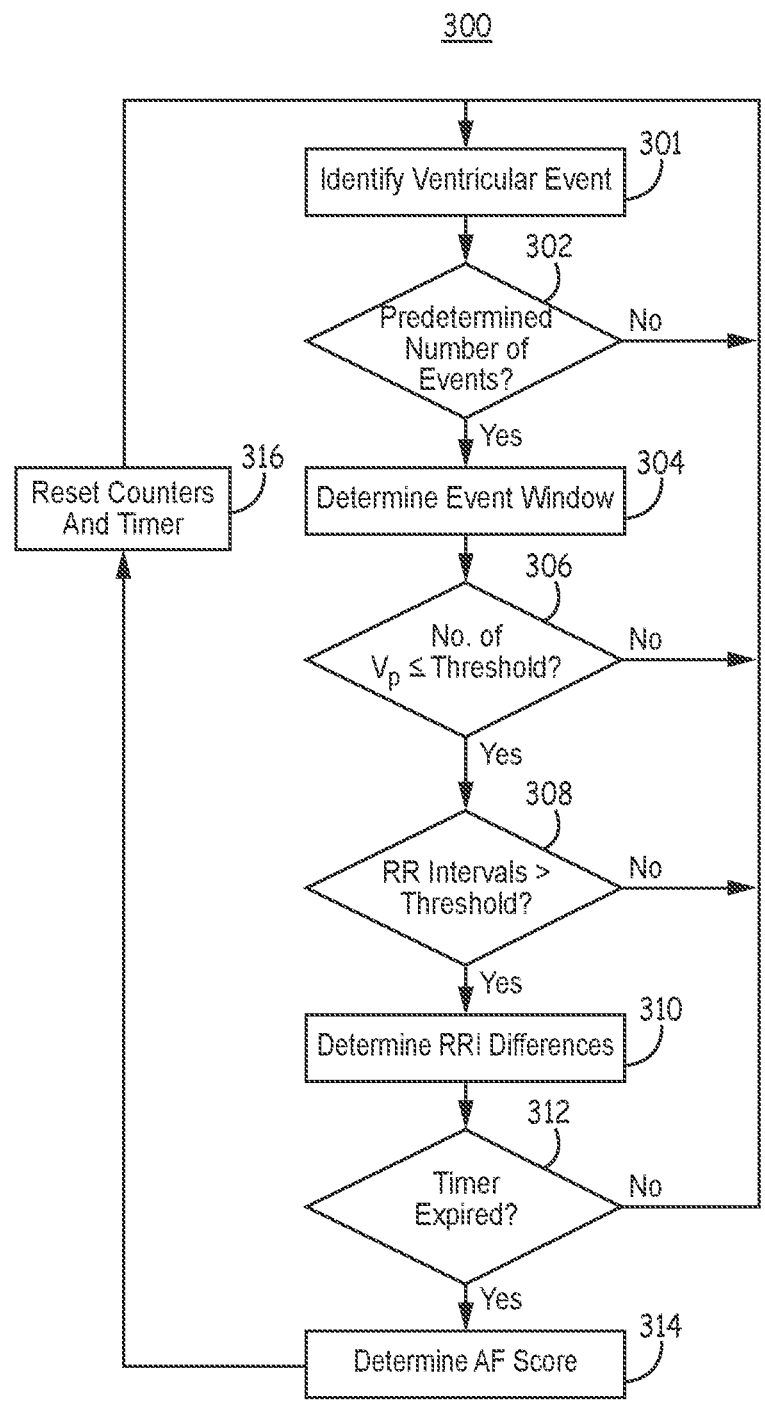
FIG. 6 is flowchart of a method for determining a factor for classifying time periods for detecting atrial tachyarrhythmia according to one example.

FIG. 6 is a flowchart 300 of a method for determining a factor for classifying time periods for detecting atrial arrhythmias according to one example. Flow chart 300 and other flow charts presented herein are intended to illustrate the functional operation of ICD 10 or another device performing the disclosed methods, and should not be construed as reflective of a specific form of software, firmware or hardware necessary to practice the methods. It is believed that the particular form of software will be determined primarily by the particular system architecture employed in the device and by the particular detection and therapy delivery methodologies employed by the device. Providing software, firmware and/or hardware to accomplish the techniques disclosed herein in the context of any modern medical device, given the disclosure herein, is within the abilities of one of skill in the art.

Methods described in conjunction with flow charts presented herein may be implemented in a non-transitory computer-readable medium that includes instructions for causing a programmable processor, such as processor 224, to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

As illustrated in FIG. 6, the processor 224 identifies ventricular events at block 301, such as R-waves based on Rout signal line 202, and identifies the ventricular event as being either an intrinsic sensed event Vs or a paced event Vp resulting from pacing being delivered by ICD 10 or 10' (or by ICD 110 or pacemaker 101). Depending upon the number of RR intervals chosen for determining RR interval differences, processor 224 determines whether a predetermined number of events, either a ventricular pacing event Vp or intrinsic ventricular sensed event VS, have been identified at block 302. For example, according to one example, if the desired number of RR intervals for determining successive RR interval differences is three, the predetermined number of events utilized in block 302 would be four events, with the four events forming a sensing window. If the predetermined number of events has not been reached, "No" branch of block 302, processor 224 determines the next ventricular event, at block 301, and the process is repeated.

Once the predetermined number of events are identified, "Yes" branch of block 302, an event window is identified based on the four events, at block 304, and a determination may be made made as to whether the number of the events in the event window that are ventricular pace Vp events is less than or equal to a predetermined pacing event threshold at block 306. For example, according to one example, the pacing event threshold is set as one so that processor 224 determines whether one or less of the identified events in the event window are ventricular pace events. If the number of identified events in the event window that are ventricular pace Vp events is not less than or equal to, i.e., is greater than, the predetermined pacing event threshold, "No" branch of block 306, processor 224 identifies the next event at block 301, and the process is repeated.

If the number of events in the event window that are ventricular pace Vp events is less than or equal to the predetermined pacing event threshold, "Yes" branch of block 306, processor 224 determines whether each of the RR intervals associated with the events in the current event window are greater than a predetermined interval threshold at block 308. For example, according to one example, processor 224 determines whether each of the RR intervals associated with the events in the event window is greater than 220 milliseconds. If each of the RR intervals associated with the events in the event window are not greater than the predetermined interval threshold, "No" branch of block 308, processor 224 identifies the next event at block 301, and the process is repeated using the next identified event and the resulting next event window.

If each of the RRIs associated with the events in the event window are greater than the predetermined interval threshold, "Yes" branch of block 308, processor 224 determines differences between successive RRIs associated with the identified events in the event window, block 310. Once the RRI differences for the current event window have been determined at block 308, to populate a Lorenz plot histogram as described above, processor 224 determines whether a predetermined time period has expired at block 312. Processor 224 may set a timer or counter to control acquisition of RRI differences over a predetermined time period at the onset of the method of flow chart 300. In one example, the predetermined time period may be set to two minutes. In other examples, the predetermined time period may be between one to five minutes. If the time period has not expired, "No" branch of block 312, processor 224 returns to block 301 to identify the next ventricular event and the process is repeated using the next event and the resulting next event window.

Once the timer has expired, "Yes" branch of block 312, processor 224 determines an AF score at block 314, based on the determined RRI differences during the predetermined time period, e.g., two minutes. The AF score may be determined as described above with respect to FIG. 5 and/or the incorporated patents. As described below in conjunction with FIG. 7, the determined AF score for the predetermined time period is used to classify the time period (and thus the cardiac signal during the time period) as an AF time period, a non-AF time period or an unclassified time period. The stored RRI differences are then cleared and all counters and timers reset at block 316. A timer set to the predetermined time period, e.g., two minutes, is reset. Processor 224 identifies the next ventricular event at block 300, and the process is repeated for the next time period using the next identified events and the next event windows.

Figure 7:
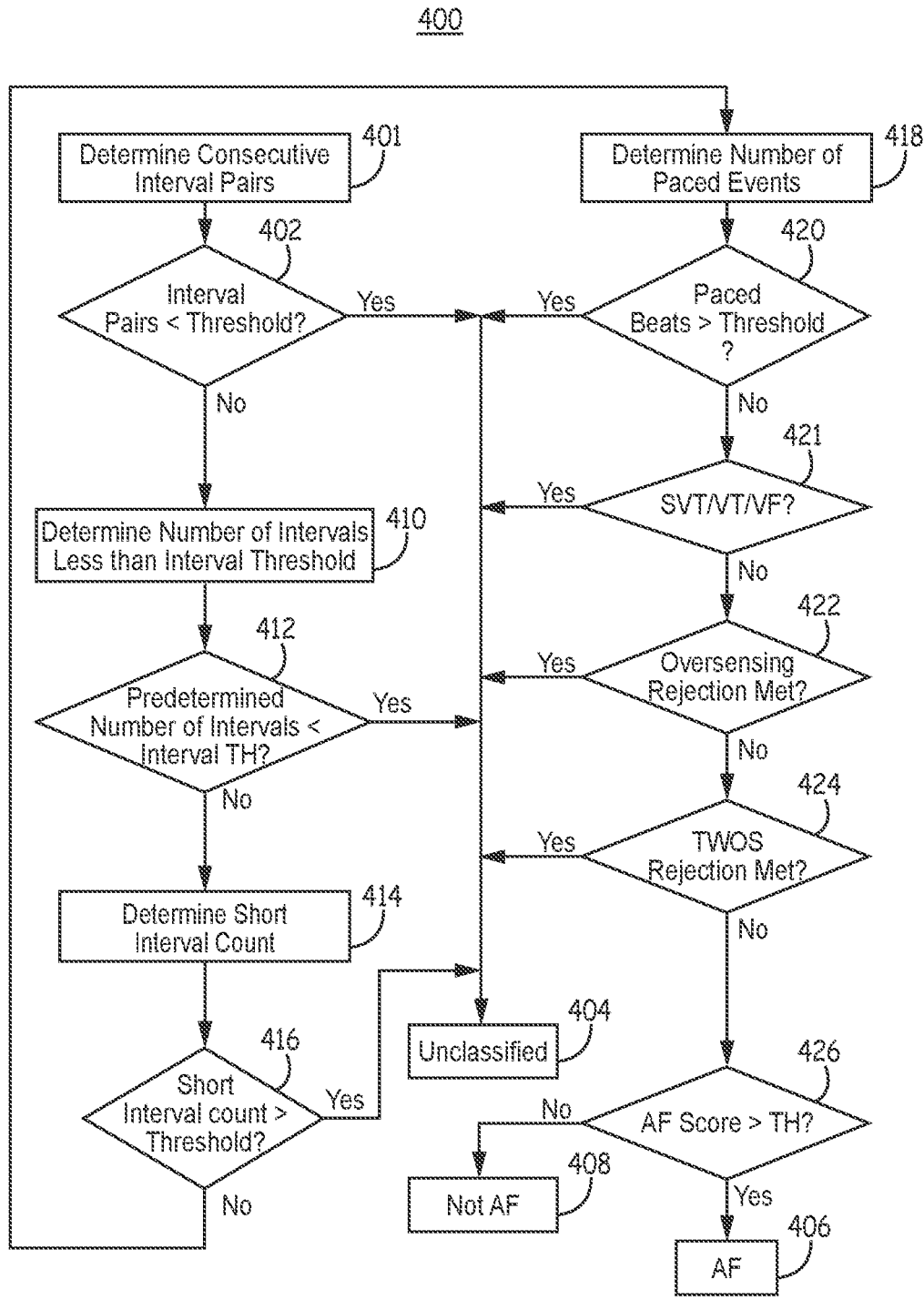
FIG. 7 is a flowchart of a method for classifying a predetermined time period for use in detecting atrial tachyarrhythmia according to one example.

FIG. 7 is a flowchart 400 of a method for classifying a predetermined time period according to one example. The example described in flowchart 400 of FIG. 7 will be described in the context of having predetermined time periods that are two minutes in length. However, the techniques described in FIG. 7 or elsewhere throughout this description can be for predetermined time periods that are longer or shorter than two minutes. Once the predetermined time period, e.g., a two minute time period, has expired and a Lorenz plot has been populated with a point associated with each determined RR interval difference determined based on the intervals in each event window occurring during the two minute time period as described in conjunction with FIGS. 4, 5 and 6, processor 224 determines whether to classify the time period as being either an AF time period, a non-AF time period, or an unclassified time period (i.e., the time period can neither be classified as an AF time period nor a non-AF time period). For example, processor 224 may analyze one or more of several factors, in any combination or particular order, to make the determination.

As described in conjunction with the example of FIG. 7, among the factors that may be analyzed for classifying the two minute time period are the number of valid RRI difference pairs, RRI lengths, number of paced beats, number of short intervals, presence of oversensing of ventricular events, presence of T-wave oversensing, detection of a ventricular tachyarrhythmia (e.g., SVT, VT or VF or more generally referred to as "other episodes"), and the AF score. However, processor 224 may analyze only a subset of these factors and/or include other factors.

Processor 224 may determine the number of RRI difference pairs acquired during the two minute time period at block 401, where each RRI difference pair represents one point of the Lorenz plot. A determination is then made as to whether the total number of RRI difference pairs formed during the two minute time period is greater than an interval pair threshold at block 402. According to one example, a threshold number of RRI difference pairs is set at 30, though other thresholds may be used. If the total number of RRI difference pairs (representing three consecutive RRIs) during the two minute time period is less than the threshold, "Yes" branch at block 402, the two minute time period is determined to be unclassified at block 404. In the example described above in which the threshold is set at 30, the "Yes" branch of block 402 means that less than 30 RRI difference pairs were determined during the two minute time period, resulting in the Lorenz plot histogram being populated with less than 30 points. An AF scored determined from fewer than the threshold number of RRI difference pairs may not yield a reliable AF score for the predetermined time period and therefore is not used to classify the time period as either AF or non-AF.

If the number of RRI difference pairs that are formed during the two minute time period is not less than the interval pair threshold (30 in the example above), "No" branch of block 402, the interval pairs factor for classifying the time period as either AF or non-AF based on an AF score determined from the RRI difference pairs is satisfied. In other words, using the example above, 30 or RRI difference pairs were determined during the two minute time period, resulting in the Lorenz plot histogram being populated with 30 or more points. The number of RRI difference pairs obtained during the pre-determined time period is adequate to reliably classify the time period as AF or non-AF based on the AF score.

According to another example, processor 224 may additionally or alternatively determine, at block 410, the total number of RRIs during the predetermined time period that were determined to be less than the interval threshold applied at block 308 of flow chart 300. If more than a threshold number of RRIs, e.g., more than a predetermined number of RRIs or a predetermined percentage of the total number of RRIs occurring during the two-minute time period, are less than the interval threshold, "Yes" branch at block 412, the two minute time period is determined to be unclassified, at block 404. If the number of RRIs less than the interval threshold does not reach or exceed a predetermined number, e.g. if less than 10 RRIs are less than the interval threshold during the two minute time period, this RRI length factor is determined not to be satisfied at block 412 ("No" branch of block 412) for classifying the predetermined time interval as unclassified. Based on at least this factor, a classification of either AF or non-AF based on the AF score is warranted.

In order to classify the two minute time period as either AF or non-AF, processor 224 may determine, at block 414, a short interval count of the total number of RRIs from all of the event windows obtained during the two minute time period that were less than or equal to a predetermined short interval threshold, such as 120 milliseconds or 130 milliseconds, for example. Processor 224 determines whether the short interval count is greater than a short interval threshold, at block 416, such as 5 short intervals for example. Too many short intervals during the two minute time period indicates the possibility of ventricular oversensing of non-physiological signals such as EMI or lead noise due to lead fracture. In this situation, the RRIs may be unreliable for determining an AF score and classifying the time period as AF or non-AF based on the AF score.

If the determined short interval count is greater than the short interval count threshold, "Yes" branch at block 416, the two minute time period is determined to be unclassified at block 404. On the other hand, if the short interval count is less than the short interval count threshold, the time period can be classified based on the AF score, "No" branch at block 416. This short interval count factor minimizes false AF detection due to lead noise oversensing.

Processor 224 may additionally or alternatively determine the number of events identified during the total two minute time period within all of the event windows that were determined to be ventricular pace Vp events at block 418. A determination is made as to whether the determined number of ventricular pace Vp events identified during all event windows of the two minute time period is greater than a total ventricular pace Vp event threshold at block 420. According to one example, the total ventricular pace Vp threshold is set as 30 ventricular pace Vp events, though other thresholds may be used.

If the number of ventricular pace Vp events during the two minute time period is greater than the total ventricular pace Vp event threshold, "Yes" branch of block 420, processor 224 classifies the two minute time period as unclassified at block 404. Ventricular pacing pulses may include bradycardia pacing pulses and/or ATP pacing pulses and may be delivered by ICD 10, 10' or 110 or by another implanted device, e.g., pacemaker 110. On the other hand, if the determined number of ventricular pace Vp events is not greater than Vp event threshold, "No" branch at block 420, the two minute time period is not classified as unclassified; a classification of AF or non-AF based on the AF score may be made as long as no other factors lead to a determination of the time period being unclassified.

Processor 224 may be configured to simultaneously evaluate R-waves and RRIs for detecting supraventricular tachycardia (SVT), VT and VF while the AF detection algorithms described herein are operating. ICD 10 may be configured to deliver therapies such as ATP in response to detecting VT. As such, if a ventricular tachyarrhythmia detection, e.g., SVT, VT or VF detection, is being made during or at the expiration of the current time period, as determined at block 421, the current time period is determined to be unclassified at block 404. If no other episode detections are being made, the process may advance to block 422.

The processor 224 may additionally or alternatively determine whether ventricular event oversensing caused by noise was detected during the two minute time period, at block 422. Detection of oversensing may be performed by processor 224 using an implemented oversensing detection scheme, such as the oversensing detection methods generally described in U.S. Pat. No. 7,333,855 to Gunderson et. al., incorporated herein by reference in its entirety. If oversensing detection criteria were met or were in the process of being met during the two minute time period, "Yes" branch of block 422, the two minute time period is determined to be unclassified at block 404. Detection of oversensing indicates that the RRIs may be unreliable for determining an AF score and classifying the time period based on the AF score. If a detection of oversensing was not made or not in the process of being made during the two minute time period, "No" branch of block 422, an AF or non-AF classification may be made based on the AF score as long as other factors do not lead to the time period be classified as unclassified.

Processor 224 may determine whether T-wave oversensing occurred during the two minute time period at block 424. The determination of T-wave oversensing may be performed by ICD 10 using an implemented T-wave oversensing detection scheme, such as the T-wave oversensing determination described in U.S. Pat. No. 7,831,304 to Gillberg, et al., incorporated herein by reference in its entirety. If a determination of T-wave oversensing was made or was in process during the two minute time period, "Yes" branch of block 424, the T-wave oversensing factor is satisfied as an indication of the two minute time period being unclassified. Processor 224 classifies the two minute time period as unclassified at block 404. If a determination of T-wave oversensing was not made or was not in the process of being made during the two minute time period, "No" branch of block 424, the T-wave oversensing factor is not satisfied. Processor 224 advances to block 426 to classify the time period based on the AF score.

In this way, ICD 10 (or ICD 10', ICD 110, or cardiac monitoring device 60) may analyze the cardiac electrical signal over the two minute time period for one or more of the described factors, which if satisfied would cause the two minute time period to be classified as "unclassified." In other words, ICD 10, ICD 110, or other device may analyze all of the described factors or only a subset of the described factors in making this determination. In some examples, if at least one the described factors for identifying the two minute time period as being unclassified is met, the two minute time period is classified as unclassified at block 404. If none of the factors evaluated in blocks 401 through 424 are determined to be satisfied according to predetermined criteria, the time period is classified as either AF or non-AF. As such, the AF score is determined based on the populated Lorenz plot histogram as described above. If the AF score is greater than an AF threshold at block 426, the two minute time period is classified as AF at block 406. On the other hand, if the AF score is not greater than the AF threshold, "No" branch of block 426, the two minute time period is classified as a non-AF at block 408.

It is understood that the determination of whether the time period is classified as unclassified (block 404), classified as AF (block 406), or classified as non-AF (block 408), may be made in any order, or at the same time, so that the determination of the two minute time period as being an unclassified time period may be used to override an initial determination of the two minute time period as being classified as AF or non-AF, or be made prior to determining the AF score for making a classification based on the AF score.

Figure 8:
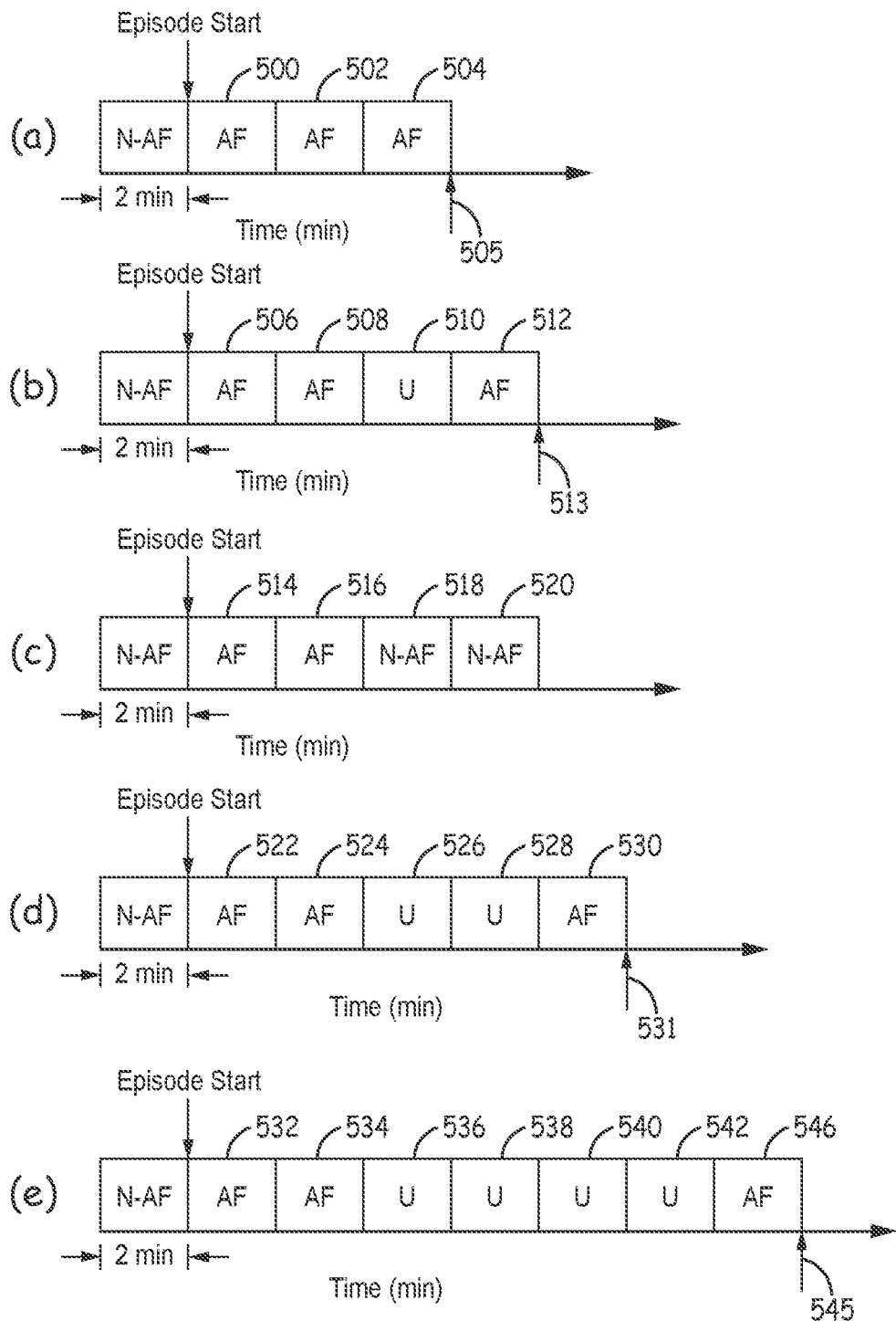
FIG. 8 is a schematic diagram of atrial fibrillation detection that may be performed by the ICDs shown in FIGS. 1A, 1B and 3A or the monitor of FIG. 1C.

FIG. 8 is a schematic diagram of atrial fibrillation detection that may be performed by a medical device according to one example. The examples described in FIG. 8 will be described in the context of having predetermined time periods that are two minutes in length. However, the techniques described in FIG. 8 can be for predetermined time periods that are longer or shorter than two minutes.

As illustrated in FIG. 8, the processor 224 classifies the cardiac signal of each two minute time period as being either AF, non-AF or unclassified using the method described in conjunction with FIG. 7. The classifications of the time periods are used to detect an AF episode. For example, once a predetermined number of two minute time periods, such as three time periods, have been classified as AF, the device detects the AF episode. Therefore, as illustrated in the scenario of timing diagram (a) of FIG. 8, once the predetermined number of two minute time periods, 500, 502 and 504, are classified as AF, processor 224 detects the AF episode at time 505. The processor 224 may track the number of two minute time periods classified as AF by updating an AF event counter each time a time period is classified as AF.

However, in the scenario illustrated in timing diagram (b), two consecutive two minute time periods 506 and 508 are classified as being AF, but the next two minute time period 510 is determined to be unclassified, followed by a subsequent time period 512 being classified as AF. According to one example, processor 224 may ignore the unclassified two minute time period 510 and detect an AF episode at time 513 once the third time period 512 is classified as AF, so that an AF episode may be detected despite one or more intermittent unclassified two minute time periods occurring between AF classifications of time periods.

In the timing diagram of scenario (b), at the identification of two minute time period 506, an AF event counter may be incremented to one. At the identification of subsequent two minute period 508, the AF event counter is incremented to two. At the identification of subsequent two minute time period 510, since the event was determined to be unclassified, the AF event counter remains at a count of two. At the classification of subsequent two minute time period 512, the AF event counter is incremented to three, and an AF episode is detected in response to the AF event counter reaching the AF detection threshold, which is 3 in this example.

As illustrated in the timing diagram of scenario (c), the classification of one or more time periods 518 and 520 as non-AF result in no detection of an AF episode. During the determination of whether the predetermined number of two minute time periods are classified as AF, the processor 224 updates the AF event counter each time an AF classification is made as described above. For example, upon classification of two minute time period 514, the AF event counter is incremented to one, and at the classification of subsequent two minute time period 514, the AF event counter is incremented to two. If two minute time period 518 were also classified as AF, processor 224 would detect an AF episode, since three two minute time periods classified as AF would have occurred, e.g. as described in the timing diagram of scenario (a) above. However, since two minute time period 518 was classified as non-AF, an AF episode detection is not made. The non-AF classification of time period 518 may be evidence that an AF episode causing AF classifications of time periods 514 and 516 is terminated or a non-sustained AF episode. In response to classifying time period 518 as non-AF, the AF event counter is reset to zero. In other examples, the AF counter may be decreased when a time period is classified as non-AF rather than immediately reset to zero.

In the timing diagram of scenario (d), at the classification of two minute time period 522 as being AF, the AF event counter is incremented to one, and at the classification of subsequent two minute time period 524 as AF, the AF event counter is incremented to two. At the classifications of subsequent two minute time periods 526 and 528, both determined to be unclassified, the AF event counter remains unchanged at a count of two. Upon classification of subsequent two minute time period 530 as being AF, the AF event counter is increased to three, and an AF episode is detected at time 531.

Had any of time periods 524, 526, 528 or 530 been classified as non-AF, the AF event counter would have been reset to zero, and the process repeated starting with the next classified two minute interval. However, in addition to resetting the AF event counter in response to a two minute time period being classified as a non-AF time period, processor 224 may also be configured to reset the AF event counter to zero if a predetermined number of two minute time periods are determined to be unclassified. For example, five consecutive two minute time periods determined to be unclassified may cause the AF event counter to be reset. In other examples, more than five or fewer than five unclassified time periods, which may not be required to be consecutive, may cause the AF counter to be decremented or reset to zero. Therefore, in the timing diagram of scenario (e), at the identification of two minute time period 532 as AF, the AF event counter is incremented to one. At the identification of subsequent two minute time period 534 as AF, the AF event counter is incremented to two. At the identification of the four subsequent two minute time periods 536, 538, 540 and 542, all determined to be unclassified, the AF event count remains unchanged at two. In the example shown, the next two minute time period 546 is classified as AF. The AF event counter is incremented from two to three, and an AF episode is detected at 545 by processor 224 in response to the AF event counter reaching the threshold count, which is three in this example.

On the other hand, if the subsequent two minute time period 546 is determined to be unclassified, the AF event counter would be reset to zero in response to a threshold number (five in this example) of consecutive unclassified time period. In the case of time period 546 being classified as a non-AF time period, the AF event counter would also be reset to zero. In either of these two cases, if the time periods 532 and 534 represent a true AF episode, the AF episode has terminated or is non-sustained as evidenced by the unclassified and/or non-AF classified time periods. The process is repeated starting with the next classified two minute interval.

Figure 9:
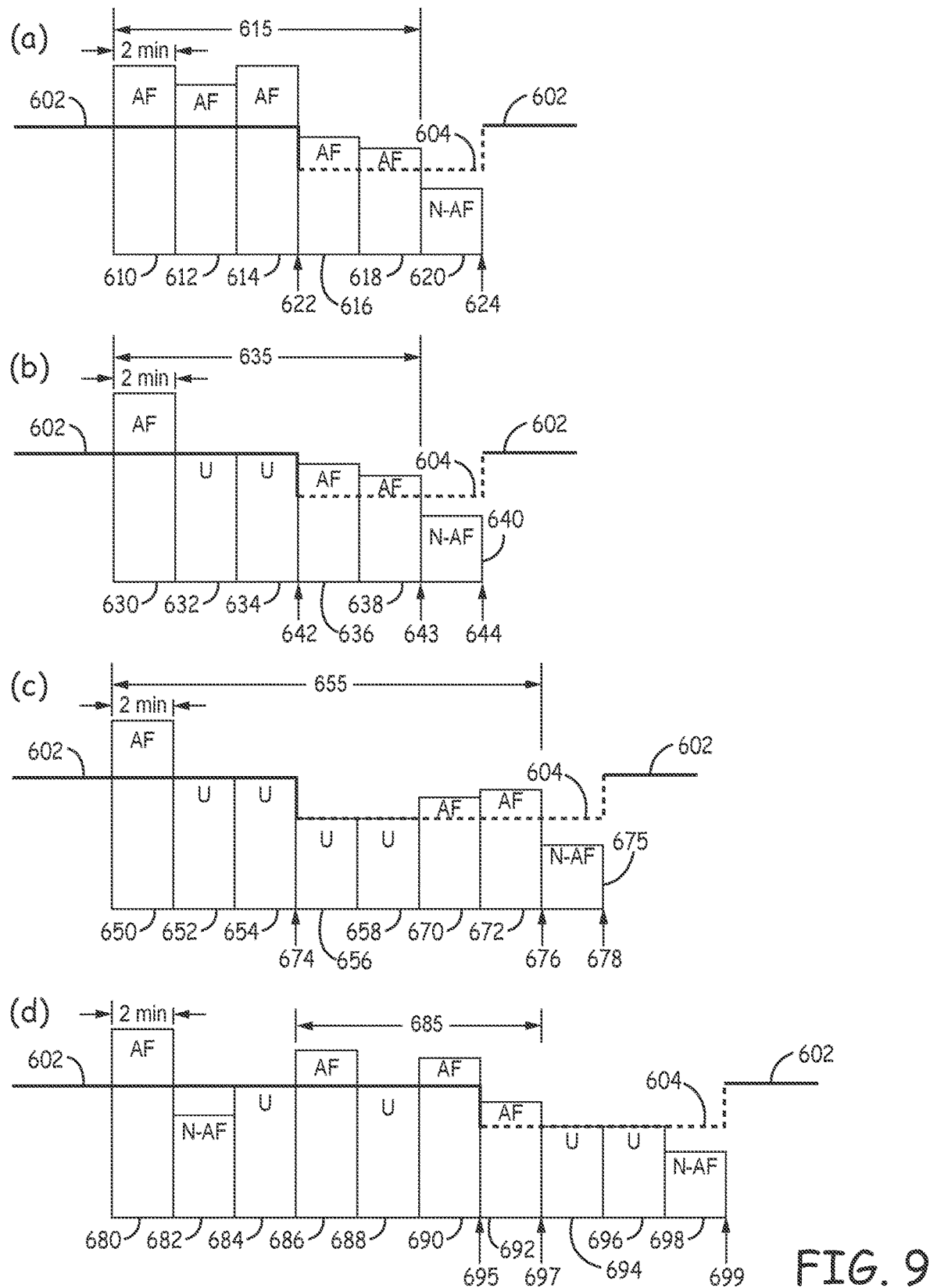
FIG. 9 is a schematic diagram of a method for detecting atrial fibrillation by an ICD or implantable monitoring device according to another example.

FIG. 9 is a schematic diagram of a method for detecting atrial fibrillation that may be performed by ICD 10 (or ICD 10', ICD 110 or cardiac monitoring device 60) according to another example. The examples described in FIG. 9 will be described in the context of having predetermined time periods that are two minutes in length and an AF detection threshold set equal to 3 time periods classified as AF. However, the techniques described may utilize different time period durations and/or different thresholds. For example, the predetermined time period may be between one to five minutes and the number of time periods classified as AF may be greater than or equal to one and less than or equal to five.

As described above, the processor 224 classifies the cardiac signal within each two minute time period as being either AF, non-AF or unclassified using the method described in conjunction with FIG. 7. If factors that cause the two minute time period to be unclassified are not satisfied, each two-minute time period is classified as AF or non-AF based on the AF score. In the method of FIG. 9, the threshold that the AF score is compared to for classifying a time period is not a fixed value but is dynamically adjusted by processor 224 in response to classifications of two-minute time periods.

For example, once a predetermined number of time periods, such as one time period, has been classified as AF based on a first AF score threshold value, if the next predetermined number of time periods are classified as any combination of AF and/or unclassified, the AF score threshold is adjusted to a second, lower value. In other words, following an initial AF classification using the first, higher AF score threshold, processor 224 decreases the AF score threshold to the second lower value at the expiration of a predetermined number of next consecutive time periods, e.g., two consecutive time periods following the initial AF classification in the examples illustrated in FIG. 9, as long as none of the predetermined number of next consecutive time periods are classified as non-AF. In other instances, the predetermined number of next consecutive time periods may be less than two, e.g., zero or one, or more than two. If any of the predetermined number of next consecutive time periods following an initial AF classification are classified as non-AF, the AF score threshold remains at the first higher threshold value.

Therefore, as illustrated in the scenario of timing diagram (a) of FIG. 9, an initial time period 610 is classified as AF based on the AF score determined for time period 610 being greater than a first AF score threshold 602 and analysis of other classification factors does not lead to an unclassified time period (as described with FIG. 7). The first AF score threshold 602 stays in effect for at least two more consecutive time periods 612 and 614 in this example. If both of these time periods are also classified as AF, in response to an AF score exceeding the first AF score threshold 602, AF is detected at time 622. Additionally, processor 224 adjusts the AF score threshold to a second, lower AF score threshold 604. The AF score of subsequent time periods will be compared to this lower threshold 604 for classifying the respective time periods.

The lower AF score threshold 604 may be set to a percentage of the initial AF score threshold 602, e.g., approximately 75% of the initial AF score. To illustrate, when the maximum possible value of the AF score is 100, the first AF score threshold may be set at 75 and adjusted to a second, lower AF score of 57. In another example, the first AF score threshold is 60 and the second is 45. In still other examples, the first AF score threshold is 60 and the second is 45, the first is 50 and the second is 38, the first is 40 and the second is 30, or the first is 25 and the second is 19. A user may program the AF score thresholds based on selection of a least sensitive, e.g. first threshold of 75 and second threshold of 57, to most sensitive, e.g., first threshold 25 and second threshold 19, with the other example given above corresponding to a less sensitive setting (first threshold 60 and second threshold 45), balanced sensitivity (first threshold 50 and second threshold 38), and more sensitivity (first threshold 40 and second threshold 30). In other examples, the actual values of the first and second thresholds may be programmable selected individually in any combination of a first range, e.g., from 25 to and including 75 for the first threshold, and a second range, e.g., from 19 to and including 57 for the second threshold, as long as the first threshold is greater than the second threshold value. In other examples, the second threshold may be set to be another percentage of the initial threshold, e.g., between 65-85%, 70-80%, or some other percentage.

By reducing the AF score for subsequent time periods, AF detection sensitivity is increased at appropriate times while AF detection specificity is maintained by using the first higher AF score threshold and applying the factors that lead to unclassified time periods. For example, the next two consecutive time periods 616 and 618 are both classified as AF based on an AF score exceeding the second threshold 604, even though the first, higher threshold 602 is not met (and factors leading to an unclassified classification are not present). The detected AF episode is detected as still being in progress during time periods 616 and 618 even though the AF scores for these time periods 616 and 618 are each less than the first threshold 602. The next time period 620 is classified as non-AF due to an AF score being less than the second threshold 604. In response to the non-AF classification, processor 224 adjusts the AF score threshold from the lower threshold 604 back to the higher threshold 602 at time 624. Termination of the AF episode is detected in response to the non-AF classification. The AF episode duration 615 is the time interval from the start of the earliest time period 610 classified as AF that led to AF detection at time 622 to the end of last AF classification time period 618 that precedes termination detection at time 624, i.e., that precedes the time period 620 classified as non-AF.

In the scenario illustrated in timing diagram (b), two consecutive two minute time periods 632 and 634 are classified as being unclassified after an initial time period 630 is classified as AF based on the first AF score threshold 602. In response to no non-AF classifications of the two time periods 632 and 634 following the initial AF classification of time period 630, processor 224 adjusts the AF score threshold at time 642 to the second lower threshold 604. Three consecutive classifications including at least an initial AF classification and no non-AF classifications cause an adjustment of the AF score threshold. As such, in one example, time periods 632 and 634 immediately and consecutively following the initial AF classified time period 630 may both be unclassified (as shown in this example), both be classified as AF, or one classified as AF and one unclassified to cause the AF score threshold to be adjusted at time 642.

Since only one time period 630 has been classified as AF in the example shown, however, an AF detection is not made at time 642 when the AF score threshold is adjusted. The next two time periods 636 and 638 are classified as AF in response to an AF score being greater than the adjusted AF score threshold 604 (and factors that would cause an unclassified classification to be made not being determined). When the AF event counter reaches a count of three at time 643, an AF detection is made. The next time period 640 is classified as non-AF in this example. Termination of the AF episode is detected, and the AF score threshold is adjusted from the lower value 604 back up to the higher value 602 at time 644 in response to the non-AF classification and resulting episode termination detection.

The episode duration 635 starts with the earliest time period 630 that was classified as AF and led to AF detection at time 643 and extends through the latest AF-classified time period 638 prior to termination detection at time 644. The episode duration 635 includes unclassified time periods 632 and 634 that do not lead to detection of termination at time 644. Unclassified time periods 632 and 634 occur between AF-classified time periods 630 and 636 and are therefore included in AF episode duration 635. The time periods 632 and 634 may be classified as unclassified due to any of the other factors described in FIG. 7. In one particular example, one or both of the time periods 632 and 634 may be classified as unclassified due to ventricular tachyarrhythmia detection (block 421 of FIG. 7). By allowing time periods 632 and 634 to be classified as unclassified when ventricular tachyarrhythmia is being detected, the detection of AF and determination of the AF episode duration 635 are uninterrupted. The detection of an AF episode that is concurrent with a ventricular tachyarrhythmia episode provides important diagnostic information for the clinician to use in properly determining the patient's heart rhythm status and subsequent treatment.

In scenario (b) and other scenarios that follow, the time periods determined to be unclassified, e.g., time periods 632 and 634 are represented as having AF scores being equal to the currently set AF score threshold. It is to be understood, however, that an actual AF score, if determined, may be greater than, equal to, or less than the current value of the AF score threshold but is not used to classify the time period when the analysis of other factors cause the time period to be determined as unclassified as described in conjunction with FIG. 7. In some cases, if the time period is determined to be unclassified due to analysis of one or more factors as described in conjunction with FIG. 7, determination of an AF score for the current time period may not be made; classification of the time period as unclassified may preclude the need to determine the AF score in some examples.

In scenario (c), the AF score threshold is adjusted from a first threshold 602 to a second threshold 604 at time 674 after an initial AF classified time period 650 based on the first, higher threshold 602 followed by two consecutive time periods 652 and 654 that do not include a non-AF classification. Processor 224 may increment an AF event counter in response to each AF classification and increment an unclassified event counter in response to each unclassified time period. Accordingly, in the example of scenario (c), at time 674 the AF event counter is at a count of one, and the unclassified event counter is at a count of two. After time period 656, the unclassified event counter is at a count of three, and after time period 658 the unclassified event counter is at a count of four. The next two time periods 670 and 672 are classified as AF based on the respective AF scores exceeding the second, lower AF score threshold 604. In some examples if the next time period 670 is also an unclassified time period, such that five unclassified time periods occur consecutively, the AF event counter and the unclassified event counter may be reset to zero, and the AF score threshold may be increased to the first, higher AF score threshold 602. Processor 224 may therefore adjust the AF score threshold and reset counters in response to detecting a predetermined number of consecutive unclassified time periods.

In the example shown, the next time period 670 is classified as AF so the unclassified event counter remains at a count of four. The AF event counter is increased to two after time period 670 and to three after time period 672. AF is detected at time 676 in response to the AF event count reaching the detection threshold, which is three in this example. The AF score threshold remains at the second, lower threshold 604 until termination of the AF episode is detected in response to a non-AF classification, e.g., time period 675, or a predetermined number of consecutive unclassified time periods, e.g., five consecutive unclassified time periods. At time 678, the AF score threshold is adjusted to the first, higher threshold 602 in response to the non-AF classification of time period 675. As shown by the example of scenarios (b) and (c), an AF episode may be detected after the AF threshold is adjusted to the second, lower threshold.

The episode duration 655 in scenario (c) begins with AF time period 650 and extends through AF time period 672 which led to AF detection at time 676. This episode duration 655 includes the consecutive unclassified time periods 652, 654, 656, and 658 which do not lead to detection of AF termination at 678.

Scenario (d) shows another example of a series of two-minute time period classifications and the corresponding adjustment to the AF score threshold. An initial time period 680 is classified as AF based on the first, higher AF score threshold 602. The AF event counter is increased to a count of one. The next time period 682 is classified as non-AF based on the first AF score threshold 604. The AF event counter may be reset to zero in response to the non-AF classification. The unclassified time period 684 may not be counted by processor 224 since the AF event counter is currently zero.

A subsequent sequence of AF-U-AF (time periods 686, 688 and 690, respectively) result in an AF event count of two and an unclassified event count of one. The two consecutive time periods 688 and 690 following the AF time period 686 which are classified as unclassified and AF, respectively, result in a combined event count of the AF and unclassified time periods being equal to three. In response to this combined event count of three, processor 224 adjusts the AF score threshold from the first, higher AF score threshold 602 to the second lower AF score threshold 604 at time 695. AF is not yet detected because the AF event count is two. The next time period 692 is classified as AF based on a comparison of the AF score to the second, lower AF score threshold 604. Processor 224 increases the AF event count to three and detects AF at time 697 in response to the AF event count reaching the detection threshold. Upon detecting AF at time 697, the unclassified event counter is reset to zero. The unclassified event counter will count unclassified time segments beginning from zero after the AF detection in order to count consecutive unclassified time periods for detecting termination of the AF episode. The unclassified event count reaches two after time periods 694 and 696. The next time period 698 is classified as non-AF resulting in detecting termination of the AF episode at time 699. All event counters are reset to zero, and the AF score threshold is adjusted back to the first, higher threshold 602 at time 699.

The episode duration 685 starts with AF-classified time period 686 which is the earliest AF classified episode that led to AF detection at time 697. The episode duration includes unclassified time period 688 which did not contribute to detection of termination at block 699. Episode duration 685 ends with the last AF-classified time period 692 prior to detecting termination at time 699. Unclassified time periods 694 and 696 may, in some instances, not be included in the episode duration 685 because they immediately precede the non-AF classified time period 698 that results in episode termination detection with no intervening AF-classified episode. In other instances, however, those unclassified time periods may also be included in the episode duration 655.

The first and second AF score thresholds may be fixed values or may be programmable by a user. In one example, a user may program the first and second AF score thresholds to be increased or set to a relatively higher value than currently programmed or decreased or set to a relatively lower value than currently programmed. Both the first and second AF score thresholds are adjusted together up or down by the same increment or decrement respectively, in response to the user-entered programming command. In other examples, a user may programmably select each of the first and second AF score thresholds tailored to individual patient need.

While only two different AF score thresholds 602 and 604 are illustrated in the example of FIG. 9, it is understood that the AF score threshold may be adjusted between three or more AF score threshold values in other examples. For instance, after AF detection is made at time 697, the AF score threshold set to the second, lower threshold 604 could be reduced to a third lowest AF score threshold to allow continuing detection of the AF episode using less stringent criteria than the initial AF detection criteria. In other examples, once the AF detection is made at time 697, the AF score threshold could be increased from the second, lower threshold 604 back up to the first, higher threshold 602 or to a third, intermediate threshold value between the second, lower threshold 604 and the first, higher threshold 602. The third intermediate threshold value may be applied for classifying subsequent time periods until termination of the AF episode is detected based on a predetermined number of time periods being classified as non-AF based on an AF score falling below the third intermediate threshold value.

In the example scenarios of FIG. 9, the AF score threshold is adjusted after at least two consecutive time period classifications of any combination of AF and unclassified immediately follow a preceding or initial AF classified time period. In the example of two minute time intervals, the AF score threshold is adjusted after six minutes with no non-AF classification. In other examples, the AF score threshold may be adjusted after fewer or more time periods. For example, a single time period classified as AF may cause the AF score threshold to be reduced to a second lower value. In other words, the AF score threshold may be adjusted immediately in response to time period 610, 630, 650, or 680 being classified as AF, e.g., immediately after the first AF classified time period. In other examples, at least one unclassified or AF time period following an immediately preceding AF time period may cause the AF score threshold to be adjusted. In still other examples, more than two time periods that are not classified a non-AF and consecutively follow a first time period classified as AF may be required before adjusting the AF score threshold. Thus, total duration from the beginning of the first time period classified as AF until the AF score threshold is adjusted may be greater than or equal to two minutes and less than or equal to ten minutes, for example.

Figure 10:
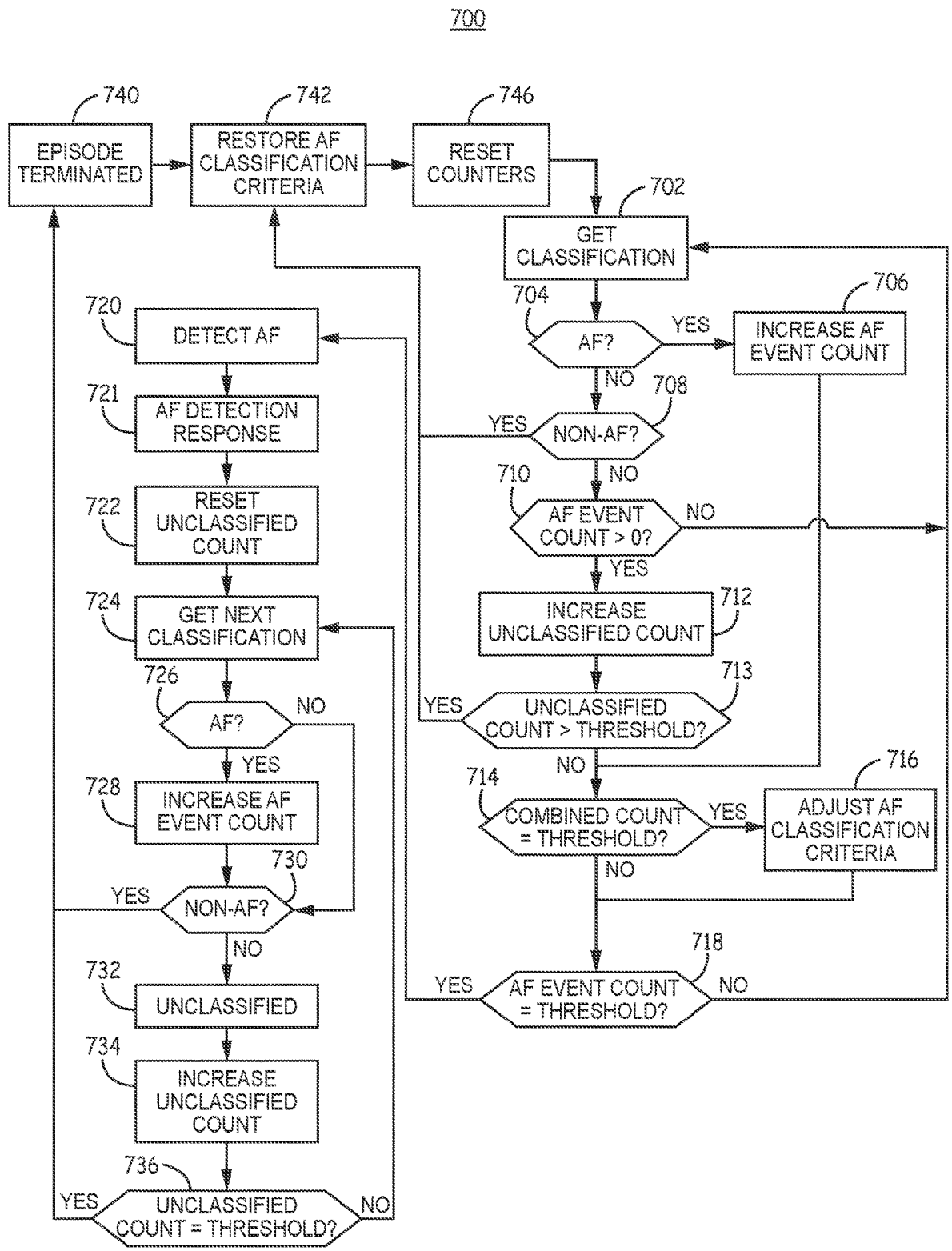
FIG. 10 is a flowchart of a method for detecting atrial fibrillation, according to one example.

FIG. 10 is a flowchart 700 of a method for detecting atrial fibrillation, according to one example. At block 702, the classification of the current time period is determined. If the classification is AF, as determined at block 704, processor 224 increases the AF event counter at block 706 and advances to block 714 to compare a combined count of the AF event counter and the unclassified event counter to a threshold. If the combined counts do not meet the threshold at block 714, the AF event count is compared to the AF detection threshold at block 718.

If the time period is not classified as AF, "No" branch of block 704, and is classified as non-AF, "Yes" branch of block 708, the processor 224 advances to block 742. The AF classification criteria, if previously adjusted, are restored to initial values. For example, if an AF score threshold has been previously adjusted to a second lower threshold, the AF score threshold is returned to a higher first threshold as described in conjunction with FIG. 9. At block 746, the AF event counter and the unclassified event counter are reset to zero if they have been previously incremented to a non-zero value.

If the current time period classification obtained at block 702 is neither AF nor non-AF, i.e., if the current time period is determined to be unclassified, "No" branch of block 708, and the AF counter is currently inactive with a value of zero, "No" branch of block 710, processor 224 determines the classification of the next time period at block 702. If the AF event count is greater than zero as determined at block 710, indicating that an initial AF classification has been made, and the current time period is unclassified, processor 224 increases the unclassified event count by one at block 712. The unclassified event count may be used for controlling adjustment of AF classification criteria prior to an AF detection being made as described in conjunction with FIG. 9. If the unclassified event count has reached a predetermined threshold, "Yes" branch of block 713, processor may restore initial AF classification criteria (if previously adjusted) at block 742 and reset the unclassified event counter and the AF event counter to zero at block 746. The process begins again at block 702 with the classification of the next time period.

After increasing the AF event count at block 706 or increasing the unclassified event count at block 712, if the unclassified event count has not reached the predetermined threshold, "No" of block 713, the combined event count may be compared to a threshold at block 714. When the combined count of the AF event counter and the unclassified event counter has reached a threshold at block 714, e.g., a combined count of three, the AF classification criteria may be adjusted at block 716. In one example, processor 224 adjusts the AF classification criteria by decreasing the AF score threshold to a second lower threshold after classifying a first time period as AF and classifying the next two consecutive time periods as any combination of AF or unclassified based on the first higher AF score threshold as described above. The AF classification criteria may therefore be adjusted in response to three consecutive time periods being classified as AF, a sequence of AF-U-AF or a sequence of AF-U-U.

It is to be understood that in some examples once the combined count reaches a predetermined threshold at block 714, and the AF classification criteria have been adjusted at block 716 prior to an AF detection being made, the AF classification criteria are not adjusted again until AF episode termination is detected, e.g., based on a time period classified as being non-AF (block 708) or based on a predetermined number of unclassified time periods (block 713), e.g., five consecutive unclassified time periods. In other examples, additional adjustments to the AF score may be made before AF episode termination is detected, e.g., to a third AF score threshold or back to the first, highest AF score threshold, as described above.

At block 718, processor 224 compares the AF event count to the AF detection threshold. When the AF detection threshold has not been reached, processor 224 returns to block 702 to obtain the next time period classification. As described above, after adjusting the AF classification criteria at block 716, if a non-AF classification is made ("Yes" branch of block 708) before detecting AF, the AF classification criteria are restored to the initial classification criteria at block 742 and all AF event and unclassified event counters are reset to zero at block 746. If subsequent time periods are classified as AF, "Yes" branch of block 704, the AF event count is increased accordingly at block 706.

If the AF event count reaches a detection threshold, "Yes" branch of block 718, processor 224 detects AF at block 720. An AF detection response is provided at block 721. The response to AF detection may include controlling pace timing and control 212 to deliver an atrial anti-arrhythmia therapy or withhold a ventricular therapy. The response to AF detection may additionally or alternatively include storing data relating to the AF episode, such as the time of onset, the total duration (as determined from the AV event counter upon detection of termination of the AF episode as discussed below or computed using the techniques described in FIG. 9), storing an episode of the cardiac electrical signal in RAM 226 and/or other data relating to the AF event. The data may be transmitted to external device 40 (FIG. 1) for displaying or communicating the data to a clinician for use in managing the patient.

When an AF detection is made at block 720, the unclassified event counter is reset to a count of zero at block 722. Processor 224 may begin counting subsequent time periods determined to be unclassified after AF detection is made for detecting termination of the AF episode. The next time period classification is obtained at block 724. If the next time period classification is AF, as determined at block 726, the AF event count is increased at block 728. AF classifications made after AF detection are based on the adjusted AF classification criteria. The AF event counter may continue to be increased with each AF classification made after detecting AF at block 720 for use in determining the duration of the AF episode and determining AF burden (e.g., the combined duration of all detected AF episodes over a given monitoring interval such as 24 hours). Such AF episode data may be transmitted to an external medical device for display or communication to a clinician thereby providing useful information to the clinician in making diagnostic and therapy management decisions.

If the classification of the next time period is not AF, "No" branch of block 726, but is non-AF, "Yes" branch of block 730, termination of the AF episode is detected at block 740. If the classification of the next time period is neither AF nor non-AF, "No" branch of block 730, i.e., if the time period is determined to be unclassified as indicated at block 732, the unclassified event counter is increased by one at block 734. The unclassified event counter is compared to a threshold at block 736. If the threshold is not reached, processor 224 returns to block 724 to fetch the next time period classification. If the unclassified count reaches a threshold at block 736, e.g., five consecutive unclassified time periods, termination of the AF episode is detected at block 740.

If episode termination is detected, the initial AF classification criteria are restored at block 742, and the AF event and unclassified event counters are reset at block 746. The process begins again at block 702.

Figure 11:
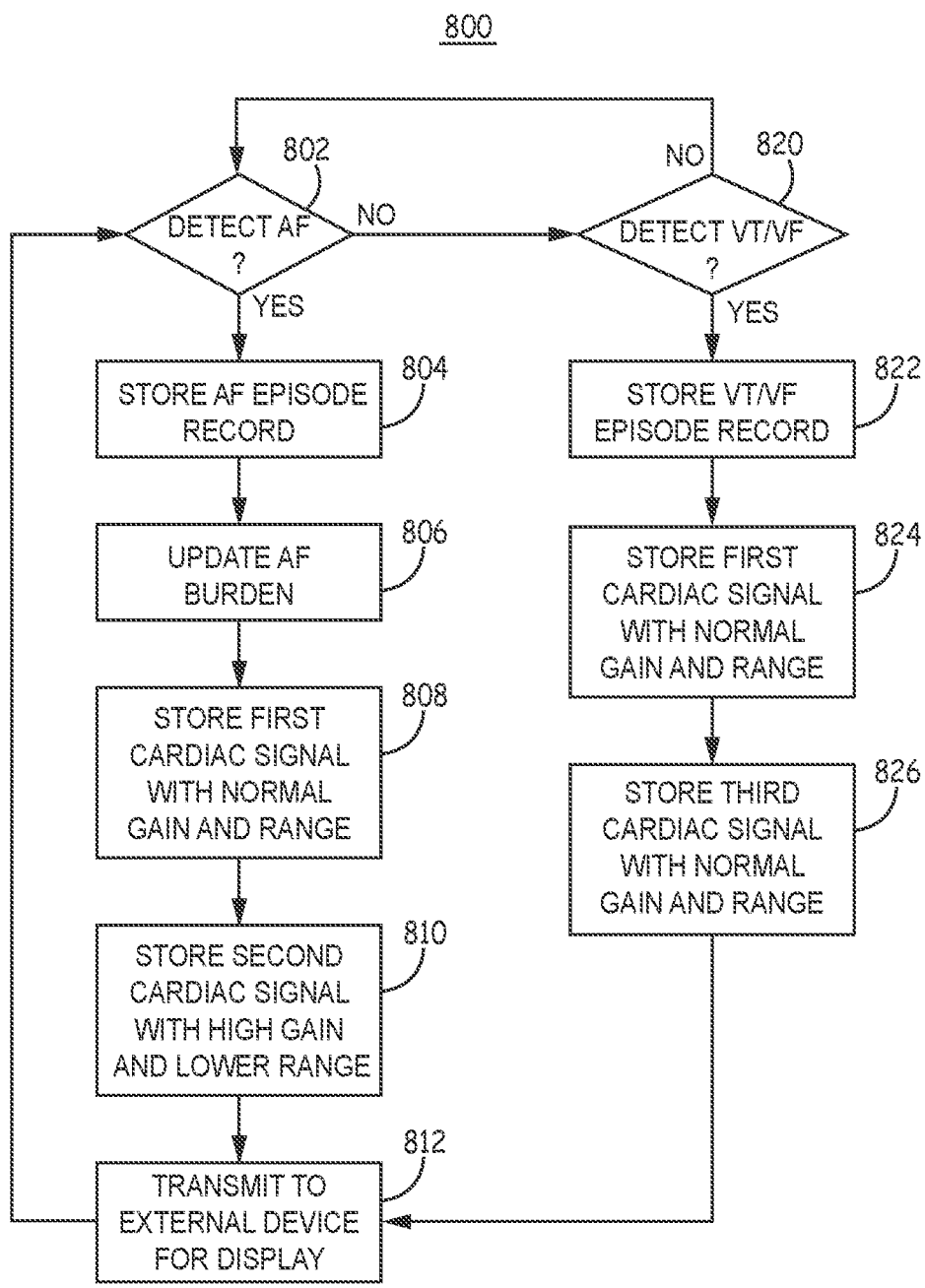
FIG. 11 is a flow chart of a method performed by an ICD or implantable monitor for providing a response to detecting atrial tachyarrhythmia according to one example.

FIG. 11 is a flow chart 800 of a method performed by ICD 10 or ICD 110 for providing a response to detecting AF according to one example. If an AF detection is made at block 802, e.g., as described in conjunction with any of FIGS. 8-10, an AF episode record is stored at block 804. The AF episode record may include a Lorenz plot or histogram of RRI data that led to AF classifications and AF detection. The episode record stored at block 804 may further include the start time, termination time, and total duration of the AF episode. Referring again to FIG. 9, examples of episode durations 615, 635, 655, and 685 are shown extending from the start of the first respective AF classified time period that led to AF detection and ending with the last AF classified time period that leads to detection of termination of the AF episode. Unclassified episodes that lead to termination detection, e.g., unclassified episodes 694 and 696 in scenario (d) may not be included in the episode duration, whereas unclassified episodes that do not immediately precede termination detection, e.g., unclassified episodes 652, 654, 656 and 658 in scenario (c), are included in the episode duration, e.g., duration 655.

When unclassified time periods are included in the AF episode or lead to termination detection of the AF episode, the factor(s) leading to determining the time period as being unclassified may be stored with the AF episode record. For example, if the time period is determined to be unclassified due to other episodes being detected such as VT or VF, due to oversensing, due to too many short RRIs, or due to too many ventricular pacing pulses during the time period, this factor may be stored to provide the clinician with useful information in diagnosing the patient's heart rhythm status for guiding therapy decisions for treating the patient's AF.

At block 806, processor 224 may determine AF burden of the patient by computed the total time AF was identified over a 24-hour time interval (or other predetermined monitoring interval). Computation of the AF burden may include counting or summing all time periods classified as AF or counting or summing only AF classified time periods that were included in a detected AF episode. AF burden may also include all unclassified time periods that occur during a detected AF episode. In some examples, unclassified time periods that lead to detecting termination of the AF episode that are not included in the AF episode duration are not included in the AF burden computation. For example, referring to FIG. 9, scenario (d), unclassified time period 684 is not included in AF burden computation because it occurs before the AF episode indicated by episode duration 685. Unclassified time period 688 is included in AF burden determination because it occurs during the AF episode. Unclassified time periods 694 and 696 are not included in determining AF burden because they lead to termination detection at time 699 and are not included in the episode duration 685.

When AF is detected, processor 224 may store a cardiac signal segment that is acquired during the detected AF episode. The cardiac signal segment is stored in memory at block 808 with the normal gain of sense amplifiers 200 and A/D converter 222 used during cardiac signal analysis and processing performed to identify RRIs, analyze the signal for oversensing, etc. For example, the cardiac signal stored at block 808 may be an EGM signal acquired using RV coil electrode 28 and ICD housing 15 in FIG. 1. In system 100 of FIG. 3A, the cardiac signal stored at block 808 may be an ECG signal acquired using defibrillation electrode 24 or defibrillation electrode 126 and housing 115. The signal stored at normal range (e.g., with 8-bit resolution sampled at 128 Hz with A/D converter input range of +12 mV) may be used to provide an unclipped EGM or ECG signal for morphology analysis (e.g., wavelet template matching) and for storing unclipped cardiac signal episodes in response to detecting a tachyarrhythmia. The normal range signal stored at block 808 may be selected as a far-field or relatively global cardiac electrical signal that is used to produce a display of the electrical rhythm of the patient's heart clearly showing R-wave morphology and regularity of RRIs for the clinician to see a high level view of the signal and the patient's corresponding rhythm. However, depending on the sensing vector, the normal range cardiac signal stored at block 808 may not include observable or easily observed P-waves.

As such, when AF is detected, the processor 224 stores a second cardiac signal in memory at block 810 with a lower range, higher gain setting, e.g., a range of +2 mV which may be controlled by adjusting the A/D converter input range. The high gain, lower range setting provides a clearer view of P-waves in the stored cardiac signal segment when displayed by external device 40. The high gain, lower range setting may result in clipping of R-waves in the stored second cardiac signal. However, the first cardiac signal stored at normal range provides a reliable, unclipped display of the R-wave morphology.

The second cardiac signal stored with a high gain, lower range setting may be selected as a second far-field or relatively global signal. For example, in system 1 of FIG. 1A or 1B, the second cardiac signal may be acquired between the RV coil electrode 24 and the SVC coil electrode 26, or the SVC coil electrode 26 to the ICD housing 15. In the system 100 of FIG. 3A, the second cardiac signal may be acquired using the sensing electrode 128 and sensing electrode 131, one of sensing electrodes 128, 130 or 131 paired with one of defibrillation electrodes 124 or 126, or one of electrodes 124, 126, 128, 130 or 131 paired with housing 115.

When ICD 10 or ICD 110 receives an interrogation command from an external device 40, processor 224 controls telemetry circuit 330 to transmit the AF episode record, AF burden information, and the stored first, normal gain cardiac signal and the second higher gain cardiac signal. The external device is configured to generate a display of the AF data for the patient to provide the clinician with valuable diagnostic information to support therapy decision-making process.

If AF is not being detected, "No" branch of block 802, processor 224 may be detecting VT or VF at block 820. If not detecting VT or VF, "No" branch of block 820, processor 224 continues monitoring for cardiac tachyarrhythmias at blocks 802 and 820. If AF is not being detected at block 802 but processor 224 is detecting VT or VF, "Yes" branch of block 820, the VT or VF episode record is stored at block 822, which may include rate, duration, start time, end time, delivered therapies and results, etc. At block 824, a segment of the first cardiac signal with normal gain acquired during the detected episode is stored. The first cardiac signal at normal gain may be a far-field or relatively global signal as described above that provides a high level view of R-wave morphology and RRIs and may be the same signal with the same gain that is stored at block 808 in response to AF detection. At block 826, a third cardiac electrical signal is stored with normal gain.

The third cardiac electrical signal may be a near-field or relatively local signal acquired with a different sensing vector than either of the first or second cardiac electrical signals stored at blocks 808 and 810. For example, the third cardiac signal stored at block 826 may be an EGM signal acquired using RV tip electrode 28 and RV ring electrode 30 in FIGS. 1A and 1B. In system 100 of FIG. 3A, the cardiac signal stored at block 826 may be an ECG signal acquired using sensing electrodes 128 and 130. The third cardiac electrical signal is stored with normal gain but is acquired using a near-field or localized ventricular sensing vector that can be used to generate a display of a high quality ventricular signal when VT or VF is detected and no atrial tachyarrhythmia is detected.

In this way, ICD 10, 10' or ICD 110 provides a unique response for storing data depending on whether an atrial tachyarrhythmia is being detected, with or without concurrent SVT, VT or VF, or a ventricular tachyarrhythmia is being detected without concurrent AF detection. Storage of a high gain cardiac electrical signal and transmission to an external device 40 at block 812 for display to a clinician provides the clinician with valuable diagnostic information relating to the detected AF episode. When the AF episode is being detected simultaneously with a ventricular tachyarrhythmia detection, the relationship between events leading to the two detections can be ascertained. However, when only a ventricular tachyarrhythmia is detected, storage and transmission of a near-field or localized ventricular signal may provide the clinician with important information regarding the ventricular rhythm.

In some examples, processor 224 responds to an AF detection by selecting which cardiac electrical signals are stored as described above and transmits the signals with normal gain and range to external device 40. Processor 52 of external device 40 may automatically generate a display on user display 54 that includes the first, high gain, low range signal for observation of P-waves and the second, normal gain, normal range signal for unclipped observation of R-waves.

Thus, an apparatus and methods have been presented in the foregoing description for detecting and responding to atrial tachyarrhythmia with reference to specific examples. It is appreciated that various modifications to the referenced examples may be made, including modifying the order of steps performed and/or modifying the combinations of operations shown in the flow charts presented herein, without departing from the scope of the following claims.

The invention claimed is:

1. A medical device, comprising:
sensing circuitry configured to sense a cardiac signal; and
processing circuitry configured to detect an atrial tachyarrhythmia episode based on the cardiac signal by:
  determining for a first time period a classification factor based on the cardiac signal sensed during the first time period;
  determining that the classification factor is greater than a first threshold;
  adjusting the first threshold to a second threshold different than the first threshold in response to the classification factor determined for at least the first time period being greater than the first threshold;
  determining, for a second time period subsequent to the first time period, the classification factor based on the cardiac signal sensed during the second time period;
  detecting an atrial tachyarrhythmia episode based on at least the classification factor determined for the first time period being greater than the first threshold; and
  detecting termination of the atrial tachyarrhythmia episode based on at least the classification factor determined for the second time period being less than the second threshold.

2. The medical device of claim 1 wherein the processing circuitry is further configured to adjust the second threshold to the first threshold in response to detecting termination of the atrial tachyarrhythmia.

3. The medical device of claim 1 wherein the processing circuitry is further configured to determine an episode duration of the detected atrial tachyarrhythmia episode beginning with the first time period and ending before the second time period.

4. The medical device of claim 3 wherein the processing circuitry is further configured to:
  classify one or more intervening time periods between the first time period and the second time period as one of unclassified or atrial tachyarrhythmia; and determine the episode duration of the detected atrial tachyarrhythmia episode by including one or more of the intervening time periods that are classified as one of unclassified or atrial tachyarrhythmia in the episode duration.

5. The medical device of claim 4 wherein the processing circuitry is further configured to determine the episode duration of the detected atrial tachyarrhythmia episode beginning with the first time period and ending before one or more intervening time periods that are classified as unclassified and immediately precede the second time period.

6. The medical device of claim 4 wherein the processing circuitry is further configured to classify an intervening time period of the one or more intervening time periods as atrial tachyarrhythmia by:
determining the classification factor for the intervening time period; and
determining that the classification factor is at least the second threshold.

7. The medical device of claim 4 wherein the processing circuitry is further configured to classify an intervening time period of the one or more intervening time periods as unclassified by one of:
determining from the cardiac signal sensed during the intervening time period that less than a threshold number of RR interval pairs occur;
determining from the cardiac signal sensed during the intervening time period that a count of short RR intervals is greater than a short interval count threshold;
determining that more than a threshold number of ventricular pacing pulses are delivered during the intervening time period;
determining from the cardiac signal sensed during the intervening time period that a ventricular tachyarrhythmia detection is being made during the intervening time period; or
detecting ventricular oversensing from the cardiac signal sensed during the intervening time period.

8. The medical device of claim 3 wherein the processing circuitry is further configured to determine an atrial tachyarrhythmia burden by determining a total combined duration of atrial tachyarrhythmia episodes detected during a monitoring time interval.

9. The medical device of claim 8 further comprising a telemetry circuit configured to transmit at least one of the episode duration and the atrial tachyarrhythmia burden.

10. The medical device of claim 8 further comprising a telemetry circuit,
the processing circuitry being further configured to determine that the atrial tachyarrhythmia burden exceeds a threshold; and
the telemetry circuit being further configured to transmit a notification that the atrial tachyarrhythmia burden exceeds the threshold.

11. A method comprising:
sensing a cardiac signal;
determining for a first time period a classification factor based on the cardiac signal sensed during the first time period;
determining that the classification factor is greater than a first threshold;
adjusting the first threshold to a second threshold different than the first threshold in response to the classification factor determined for at least the first time period being greater than the first threshold;
determining, for a second time period subsequent to the first time period, the classification factor based on the cardiac signal sensed during the second time period;
detecting an atrial tachyarrhythmia episode based on at least the classification factor determined for the first time period being greater than the first threshold; and
detecting termination of the atrial tachyarrhythmia episode based on at least the classification factor determined for the second time period being less than the second threshold.

12. The method of claim 11 further comprising adjust the second threshold to the first threshold in response to detecting termination of the atrial tachyarrhythmia.

13. The method of claim 11 further comprising determining an episode duration of the detected atrial tachyarrhythmia episode beginning with the first time period and ending before the second time period.

14. The method of claim 13 further comprising:
classifying one or more intervening time periods between the first time period and the second time period as one of unclassified or atrial tachyarrhythmia; and
determining the episode duration of the detected atrial tachyarrhythmia episode by including one or more of the intervening time periods that are classified as one of unclassified or atrial tachyarrhythmia in the episode duration.

15. The method of claim 14 further comprising determining the episode duration of the detected atrial tachyarrhythmia episode beginning with the first time period and ending before one or more intervening time periods that are classified as unclassified and immediately precede the second time period.

16. The method of claim 14 further comprising classifying an intervening time period of the one or more intervening time periods as atrial tachyarrhythmia by:
determining the classification factor for the intervening time period; and
determining that the classification factor is at least the second threshold.

17. The method of claim 14 further comprising classifying an intervening time period of the one or more intervening time periods as unclassified by one of:
determining from the cardiac signal sensed during the intervening time period that less than a threshold number of RR interval pairs occur;
determining from the cardiac signal sensed during the intervening time period that a count of short RR intervals is greater than a short interval count threshold;
determining that more than a threshold number of ventricular pacing pulses are delivered during the intervening time period;
determining from the cardiac signal sensed during the intervening time period that a ventricular tachyarrhythmia detection is being made during the intervening time period; or
detecting ventricular oversensing from the cardiac signal sensed during the intervening time period.

18. The method of claim 13 further comprising determining an atrial tachyarrhythmia burden by determining a total combined duration of atrial tachyarrhythmia episodes detected during a monitoring time interval.

19. The method of claim 18 further comprising transmitting at least one of the episode duration and the atrial tachyarrhythmia burden.

20. The method of claim 6 further comprising:
determining that the atrial tachyarrhythmia burden exceeds a threshold; and transmitting a notification that the atrial tachyarrhythmia burden exceeds the threshold.

21. A non-transitory, computer-readable medium comprising a set of instructions that when executed by processing circuitry of a medical device cause the medical device to:
sense a cardiac signal;
determine for a first time period a classification factor based on the cardiac signal sensed during the first time period;
determine that the classification factor is greater than a first threshold;
adjust the first threshold to a second threshold different than the first threshold in response to the classification factor determined for at least the first time period being greater than the first threshold;
determine, for a second time period subsequent to the first time period, the classification factor based on the cardiac signal sensed during the second time period;
detect an atrial tachyarrhythmia episode based on at least the classification factor determined for the first time period being greater than the first threshold; and
detect termination of the atrial tachyarrhythmia episode based on at least the classification factor determined for the second time period being less than the second threshold.

* * * * *